(12) United States Patent
Bhansali et al.

(10) Patent No.: US 9,121,806 B1
(45) Date of Patent: Sep. 1, 2015

(54) IMPEDANCE SPECTROSCOPY-BASED CELLULAR ANALYSIS DEVICE

(75) Inventors: Shekhar Bhansali, Tampa, FL (US); Abdur Rub Abdur Rahman, Tampa, FL (US)

(73) Assignee: University of South Florida, Tampa, FL (US)

( * ) Notice: Subject to any disclaimer, the term of this patent is extended or adjusted under 35 U.S.C. 154(b) by 1478 days.

(21) Appl. No.: 12/180,982

(22) Filed: Jul. 28, 2008

Related U.S. Application Data

(60) Provisional application No. 60/962,306, filed on Jul. 26, 2007.

(51) Int. Cl.
| | | |
|---|---|---|
| *C12M 1/34* | (2006.01) | |
| *G01N 27/02* | (2006.01) | |
| *G01N 33/483* | (2006.01) | |
| *G01N 33/543* | (2006.01) | |
| *A61B 5/145* | (2006.01) | |

(52) U.S. Cl.
CPC .............. *G01N 27/02* (2013.01); *A61B 5/145* (2013.01); *G01N 33/4836* (2013.01); *G01N 33/54366* (2013.01); *G01N 33/54373* (2013.01)

(58) Field of Classification Search
CPC .............. A61B 5/145; G01N 33/4836; G01N 33/54366; G01N 33/54373; B01J 2219/00722; B01J 2219/0046; B82Y 30/00
USPC .............................. 435/285.2, 287.2; 600/547
See application file for complete search history.

(56) References Cited

U.S. PATENT DOCUMENTS

| | | | | |
|---|---|---|---|---|
| 3,890,201 A | * | 6/1975 | Cady ........................... | 435/287.1 |
| 3,968,487 A | * | 7/1976 | Herring et al. ................ | 341/141 |
| 5,187,096 A | * | 2/1993 | Giaever et al. ............. | 435/287.1 |
| 5,306,414 A | * | 4/1994 | Glass et al. .................... | 204/404 |
| 6,051,422 A | * | 4/2000 | Kovacs et al. ............... | 435/287.1 |
| 6,099,803 A | * | 8/2000 | Ackley et al. ................ | 422/68.1 |
| 6,169,394 B1 | | 1/2001 | Frazier et al. | |
| 6,482,619 B1 | | 11/2002 | Rubinsky et al. | |

(Continued)

OTHER PUBLICATIONS

Hofmann et al. "Galvanically decoupled impedance spectroscopy for biological high-throughput-scrreening in micortiter plates". Sensors. IEEE. Oct. 30, 2005. pp. 1157-1160.*

(Continued)

*Primary Examiner* — Michael Hobbs
(74) *Attorney, Agent, or Firm* — Robert J. Varkonyi; Smith & Hopen, P.A.

(57) ABSTRACT

An electrical impedance sensing device which integrates multielectrode automated impedance spectroscopy capability with automatic parameter extraction and data analysis to create an automated cell behavior monitoring system. The device comprises radial electrodes and an out-of-plane counter electrode. Quantitative impedance data provided information on cell adhesion, spreading, proliferation and detachment due to cell cycle processes as well as cell-drug interaction, with spatio-temporal resolution. The resulting dataset is processed for impedance distribution and used to characterize cellular motion, morphology, electrochemical and dielectric properties. Also, a method is described for studying cell-cell and cell-matrix interactions, determining electrical characteristics of cell layers, and identifying specific impedance parameters for cancer screening, drug screening, bacterial growth monitoring, organ transplant compatibility, and cell-drug interaction among other applications.

23 Claims, 19 Drawing Sheets

(56) References Cited

U.S. PATENT DOCUMENTS

| | | | |
|---|---|---|---|
| 6,927,049 B2 | | 8/2005 | Rubinsky et al. |
| 6,977,033 B2 * | | 12/2005 | Becker et al. ............ 204/450 |
| 2003/0009112 A1 * | | 1/2003 | Hammerle et al. ......... 600/547 |
| 2004/0053290 A1 * | | 3/2004 | Terbrueggen et al. ......... 435/6 |
| 2004/0079652 A1 | | 4/2004 | Vreeke et al. |
| 2005/0059105 A1 | | 3/2005 | Alocilja et al. |

OTHER PUBLICATIONS

U. Egert, B. Schlosshauer, S. Fennrich, W. Nisch, M. Fejtl, T. Knott, T. Mueller, H. Haemmerle. "A novel organotypic longer-term culture of the rat hippocampus on substrate-integrated multielectrode arrays." Brain Research Protocols. vol. 2, pp. 229-242, 1998.*

A R A Rahman, J Register, G Vuppala and S Bhansali "Cell culture monitoring by impedance mapping using a multielectrode scanning impedance spectroscopy system." Physiol. Meas. 29. Jun. 10, 2008. pp. S227-S239.

Rahman et al. 2007. "Effect of Electrode Geometry on the Impedance Evaluation of Tissue and Cell Culture." Sensors and Actuators B. vol. 127. pp. 89-96.

Rahman et al. 2008. "Cell Culture Monitoring by Impedance Mapping Using a Multielectrode Scanning Impedance Spectroscopy System (CellMap)." Physiol. Meas. vol. 29. pp. s227-s239.

Benjamin et al. 2005. "A Planar Micro-Sensor for Bio-Impedance Measurements."Sensors and Actuators B. vol. 111-112. pp. 430-435.

Rahman et al. 2006. "A Micro-electrode Array Biosensor for Impedance Spectroscopy of Human Umbilical Vein Endothelial Cells." Sensors and Actuators B. vol. 118. pp. 115-120.

* cited by examiner

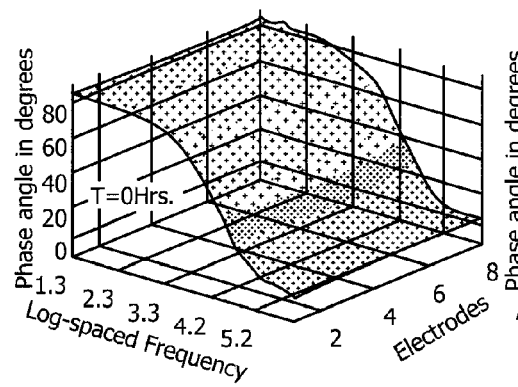
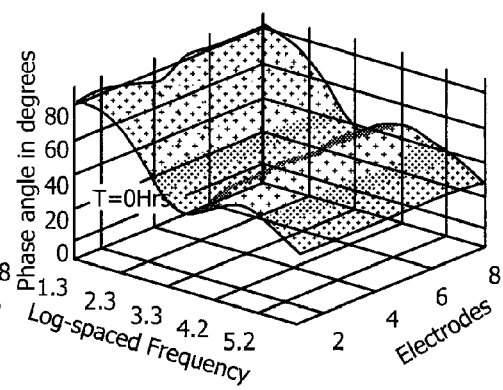
FIG. 17A          FIG. 17B
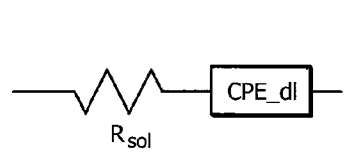
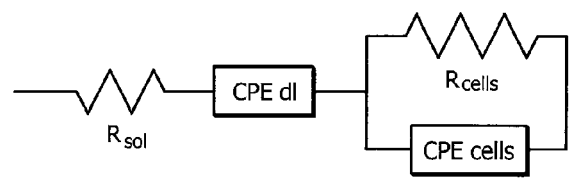
FIG. 18A          FIG. 18B

IMPEDANCE SPECTROSCOPY-BASED CELLULAR ANALYSIS DEVICE

CROSS REFERENCE TO RELATED APPLICATIONS

This application claims priority to U.S. Provisional Patent Application 60/962,306, entitled, "Cell Map: An Automated Multielectrode Array Cell Culture Analysis System Based on Electrochemical Impedence Spectroscopy", filed Jul. 26, 2007, the contents of which are herein incorporated by reference.

STATEMENT OF GOVERNMENT SUPPORT

This invention was made with Government support under Grant No. 2106-0375-00 awarded by the National Science Foundation (NSF). The Government has certain rights in the invention.

FIELD OF INVENTION

This invention relates to cellular analysis devices. More specifically, this invention relates the use of an impedence-based cellular analysis device.

BACKGROUND OF THE INVENTION

The methods employed to study cell-substrate interaction can be classified into three major categories; microscopic methods, including fluorescent microscopy, interference reflection microscopy, scanning electron microscopy, digital holographic microscopy, surface plasmon resonance microscopy, and acoustic microscopy; biochemical methods, including receptor-ligand interactions; and spectroscopic methods, including nuclear magnetic resonance and electrical impedance spectroscopy. These techniques can be broadly classified as either label- and reporter-based or label-free. Label- and reporter-based technologies require elaborate sample preparation, pre- and post-treatment. Label-free technologies are preferred due to their non-invasiveness and non-interference with biological functions.

Among the several classes of cell-based biosensors, impedemetric sensors provide a non-invasive and label-free method for monitoring cell cultures (Abassi, Y. A., et al., *Label-free, real-time monitoring of IgE-mediated mast cell activation on microelectronic cell sensor arrays*. J Immunol Methods, 2004. 292(1-2): p. 195-205). The feasibility of impedemetric sensors has been demonstrated for a variety of applications including wound healing, cell-drug interaction and apoptosis (Yin, H., et al., *Bioelectrical Impedance Assay to Monitor Changes in Aspirin-Treated Human Colon Cancer HT-29 Cell Shape during Apoptosis*. Analytical Letters, 2007. 40(1): p. 85-94; Harrison, D. J., et al., "*From micromotors to micro fluidics the blossoming of micromachining technologies in chemistry, biochemistry, and biology,*". Proc Transducers. 99: p. 7-10.). Electrical impedance-based techniques offer several advantages over microscopic techniques, such as non-invasiveness, non-destructive characteristics, label free characteristics, real-time characteristics, and dynamic monitoring of cell culture systems. However, current impedance-based whole-cell biosensors technology suffers from a lack of spatial resolution, non-specific, non-parameterized quantitative descriptors of adhesion and motility, and limited data processing and analysis capabilities.

Many abnormal cell types exhibit adhesion and proliferation characteristics that are different from their normal counterparts (Buehring, G. C. and R. R. Williams, *Growth Rates of Normal and Abnormal Human Mammary Epithelia in Cell Culture*. Cancer Res, 1976. 36(10): p. 3742-3747). To distinguish these behavioral characteristics, a space and time resolved measurement system is needed. Current real-time impedance-based cell substrate sensors use non-specific space-averaged quantitative descriptors to represent cell substrate interaction and often do not characterize the cell layer (Yu, N., et al., *Real-time monitoring of morphological changes in living cells by electronic cell sensor arrays: an approach to study G protein-coupled receptors*. Anal Chem, 2006. 78(1): p. 35-43; Peters, M. F., et al., *Evaluation of Cellular Dielectric Spectroscopy, a Whole-Cell, Label-Free Technology for Drug Discovery on Gi-Coupled GPCRs*. J Biomol Screen, 2007). Although these descriptors provide some measure of the cellular activity, the exact nature of the cell-substrate interactions is unclear. Further, a primary hurdle in distributed impedance mapping is the additional hardware requirement of switching between electrodes without introducing measurement parasitics. Additionally, data collection, processing, analysis and visualization are difficult to implement and integrate for large multidimensional datasets, especially in a real-time environment.

Real-Time Cellular Electronic Sensing (RT-CES™), manufactured by ACEA Biosciences, is a cell culture monitoring device based on a microelectronic cell sensor array integrated into the bottom of standard format micro-titre plates. RT-CES™ measures electrical impedance across the sensors to detect the presence, absence, or change in condition of cells (Matthew, A., *Current biosensor technologies in drug discovery*. Drug Discovery, 2006: p. 69). The CellKey™ System (MDS Sciex) uses cellular dielectric spectroscopy (CDS) to quantitatively and kinetically measure endogenous cell surface receptor responses to ligands in live cells. A series of receptor-specific, frequency-dependent impedance patterns, resulting from changes in cellular bio impedance are collected every two seconds as spectrum of frequencies (1 KHz to 10 MHz) (Ciambrone, G. J., et al., *Cellular Dielectric Spectroscopy: A Powerful New Approach to Label-Free Cellular Analysis*. Journal of Biomolecular Screening, 2004. 9(6): p. 467). Legendre Polynomial fitting is used to fit the difference between control and ligand initiated impedance data.

A major challenge in IS is in the interpretation of the impedance spectra. IS data is predominantly interpreted by parameter extraction via equivalent circuit modeling. Traditional spectroscopic measurements involve few datasets which are fit to circuits of choice to extract parameters. An impedance recording of cell cultures and tissues is either determined by differential impedance or absolute impedance. In differential recording, a blank or control sample is measured and compared with the impedance (or part of it) of the analyte (Huang, X., et al., *Impedance based biosensor array for monitoring mammalian cell behavior*. Sensors, 2003. Proceedings of IEEE, 2003. 1). In this approach, the absolute electrical properties are unknown and only their deviations act as markers for variability. In the second category, absolute electrical properties of cells are recorded, with the view of characterizing a particular type of cell in terms of its electrical characteristics such as complex conductivity and permittivity (Asami, K., *Dielectric dispersion in biological cells of complex geometry simulated by the three-dimensional finite difference method*. J. Phys. D: Appl. Phys, 2006. 39: p. 492-9).

Although cell-substrate studies are capable of detecting micromotion of cells (Giaever, I. and C. R. Keese, *Micromotion of Mammalian Cells Measured Electrically*. Proceedings of the National Academy of Sciences, 1991. 88(17): p. 7896-

7900), the observed impedance changes are an averaged effect of cellular motion over a large electrode area (compared to the cellular dimensions of approximately 30 µm). Moreover, the parameter describing the cell micromotion is non-specific. For example, due to the cell's close approach to the interface, the electrical double layer capacitance is modified, this is a specific quantifier because it refers to a particular aspect of cell-substrate interface. The existing methods quantify the cell-substrate interaction in terms of normalized resistance (Keese, C. R., et al., *A biosensor that monitors cell morphology with electrical fields*. Engineering in Medicine and Biology Magazine, IEEE, 1994. 13(3): p. 402-408) or a cell index (Yu, N., et al., *Real-time monitoring of morphological changes in living cells by electronic cell sensor arrays: an approach to study G protein-coupled receptors*. Anal Chem, 2006. 78(1): p. 35-43) (non-specific quantifiers), not in terms of changes in interfacial capacitance or cell-junctional resistance (specific quantifiers). With currently available impedance-based cell-substrate sensing methods, it is not possible to predict the directionality of cell growth and the cell density distribution, which are important indicators of "orderliness" of growth which in turn is an important distinction between normal and cancer cells (Schwartz, D. R., et al., *Gene Expression in Ovarian Cancer Reflects Both Morphology and Biological Behavior, Distinguishing Clear Cell from Other Poor-Prognosis Ovarian Carcinomas*. Cancer Res, 2002. 62(16): p. 4722-4729; Szent-Gyorgyi, A., *The Living State and Cancer*. PNAS, 1977. 74(7): p. 2844-2847).

Contemporary systems lack the capability for real-time impedance mapping and parameterization of evolving cell cultures and provide only an aggregate quantity measured over either a single frequency or a group of frequencies to represent cell-substrate interactions. A system is needed which can monitor specific parameters of cell-substrate interactions (e.g. cell-substrate separation) and cell-cell interactions (e.g. tight junctional resistance) on a real-time basis. A multiple electrode system performing impedance spectroscopy in real-time generates large datasets, where each electrode data has to be individually fit to an equivalent circuit for parameter extraction. This task is cumbersome unless automated. However, no such system has been reported yet that can perform real-time impedance mapping and automated parameter extraction from impedance data of time evolving cell cultures. A key challenge in the implementation of automated parameterization of evolving cell cultures is that the model representing the system continuously changes.

SUMMARY OF THE INVENTION

The present invention allows for space- and time-resolved cellular behavior and cell layer characterization in a fully automated environment. The device uses an impedance measurement instrument, a PCB-based multielectrode device with an out-of-plane counter electrode, a switching circuit and computer programming to achieve fully automated, spatially distributed impedance mapping of cell behavior and properties. Additionally, a glass cylinder was attached to the substrate of the device. The key features of this system are 1) automated impedance data acquisition 2) data analysis and visualization, and 3) automated parameter extraction. This system was employed to study the adhesion, spreading, motility, confluence and detachment of cancer cells. The present system can be implemented using any 2 port impedance measurement equipment.

A planar fabricated 8-electrode radial array with an out-of-plane counter electrode was designed and fabricated, using electrode sizes ranging from 50 µm to 500 µm. In some embodiments, the electrode have a diameter of 500 µm, 250 µm, 100 µm, or 50 µm. Electrode geometry on the impedance measurements was analyzed using simple binary electrolyte (KCl), a highly viscous conductive gel (Spectra 360™), OVCA429 ovarian cancer cell cultures and excised human skin tissue. A 2D impedance map was constructed during the period of cell adhesion and growth and confluence. The outputs of this device are color-mapped time-varying impedance images and quantitative markers which reveal the rate of cell growth, time to confluence, cell density and uniformity, properties of tight-junctions, and trans-monolayer properties.

The invention also envisions an increased number of Working Electrodes (WEs') without introducing much parasitics. This is possible due to the out of plane positioning of Counter Electrode (CE), which ensures that the gap between each working electrode and counter electrode is the same.

The impedance measurement instruments envisioned are commercial devices and small-footprint card-based impedance analyzers. The device may further be used in remote monitoring by using a portable impedance measurement unit with an integrated switching mechanism and wireless data transfer.

Cells were cultured in the device's cloning cylinder and impedance measured across all the electrode pairs at set frequency points. The impedance data was then processed through software routines to create a superimposed image of impedance from all electrode pairs in a single scan. A collection of such data from a single sweep is termed as a "frame". Based on data from consecutive frames, information such as cell adhesion, spreading, confluence, detachment, and motility was extracted.

Parameters of cell-substrate and cell-cell interactions such as interfacial capacitance, tight junctional resistance and cell layer capacitance were analyzed as a function of culture time. Tight-junctional resistance increases as a function of culture time until the cell layer attains confluence, and decreases thereafter. Constant Phase Element (CPE) and its power factor exhibited similar trends, showing a non-uniform cell distribution in the early stage of the cell culture (<30 hours), which was visually confirmed from the shape of the phase angle curve. At around the known time of confluence the cell layer parameters attain similar values on all eight electrodes, indicating confluence.

Data from the device may be processed using a computerized program. Such programs include APL, acslX, Baudline, COMSOL™, DADiSP™, Euler, FREEMAT™, GAUSS™, CNU, IDL, IGOR™, IML, LABVIEW™, Lush, MATLAB™, PAW™, Portable Extensible Toolkit for Scientific Computation, PSPP™, R™, RLAB™, and TRILINOS™ or programs developed from open-sourced languages such as C++ and JAVA for data processing and visualization.

BRIEF DESCRIPTION OF THE DRAWINGS

For a fuller understanding of the invention, reference should be made to the following detailed description, taken in connection with the accompanying drawings, in which:

FIGS. 17(*a*) and (*b*) depict phase angle as a function of frequency and electrode positions of (a) control and (b) OvCa culture. The experimental data are fitted with an equivalent circuit shown in (a) FIGS. 16(*a*) and (*b*) FIG. 16(*b*).

FIGS. 18(*a*) and (*b*) depict the circuits used to model the impedance of electrode-electrolyte impedance in (a) the absence of cells and (b) the presence of cells. Rs indicates the solution resistance, Qdl is the magnitude of constant phase element (CPE) representing double-layer effects, and ndl is the power factor of the double-layer CPE. The parameters for the models are (a) (Rs=0.584×103; Qdl=0.8268×10-8, ndl=0.9344) and (b) (Rs=0.444×103, Qdl=0.9215×10-8, ndl=0.9468, Rcell=10.38×103, Qcell=0.2175×10−10, ncell=0.6740). In addition to the electrode-electrolyte impedance, three more parameters are required to achieve a good fit between data and model; these parameters are Rcell, the cell-layer resistance, Qcell, the magnitude of the cell-layer CPE and ncell, the power factor of the cell-layer CPE.

DETAILED DESCRIPTION OF THE PREFERRED EMBODIMENT

Figure 1:
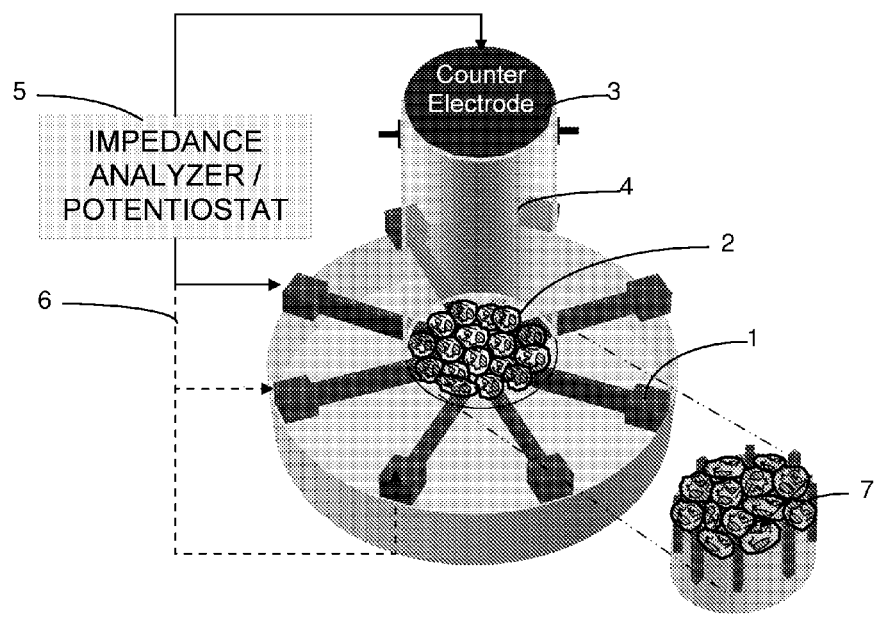
FIG. 1 depicts an illustration of the proposed 8-electrode CellMap device.

The micro-electrode devices use electrodes (1) of 5000 μm in length and 50 μm in width, were fabricated using photolithography and micromachining techniques. Out of the total length of the electrode approximately 2500 μm is in contact with the electrolyte inside cell culture cylinder (4). The electrode array fabrication is a single mask liftoff process. PY 3000 negative resist is spun onto a 2-inch glass substrate wafer. An electrode mask is used to expose the photoresist to make molds for the electrodes. Chromium (250 Å, 30 nm) was deposited onto the glass wafer followed by a gold layer (1400 Å, 100 nm) using thermal evaporation, and coated in S1813 positive photoresist. The chromium layer serves as an adhesion promoter between the glass surface and gold. The electrodes (1) were electroplated with gold to an average thickness of approximately 1.7 μm, and solvent cleaned. Another photolithography process was performed to define the 4 different electrode areas (electrode tips). The average gold thickness on the tips was approximately 4 μm. Each one of the eight electrodes serves as an independent working electrode during multielectrode scanning. After removing the Cr/Au seed layer, 2 layers of S1813 resist were spun using photolithography to covers all other areas of the device except the contact pads and the electrode tips. The resultant electrodes comprise a 1000° thickness of gold. Liftoff is performed to isolate the electrodes. This is the process flow for the 8-electrode device on glass substrate, illustrated in FIG. 1.

Counter electrode (3) of much larger surface area than the working electrodes was manufactured by electroplating gold on a group of five soldered brass cylinders of 1 mm diameter and 0.5 cm length each. The thickness of electroplated gold on the brass cylinders was approximately 5 μm. This created a large counter electrode surface area in comparison with the working electrode area. Such an arrangement of counter and working electrodes minimizes the impedance contribution of the counter electrode to the overall impedance of the bipolar system and thus simplifies the data analysis and parametrization procedures.

Figure 2:
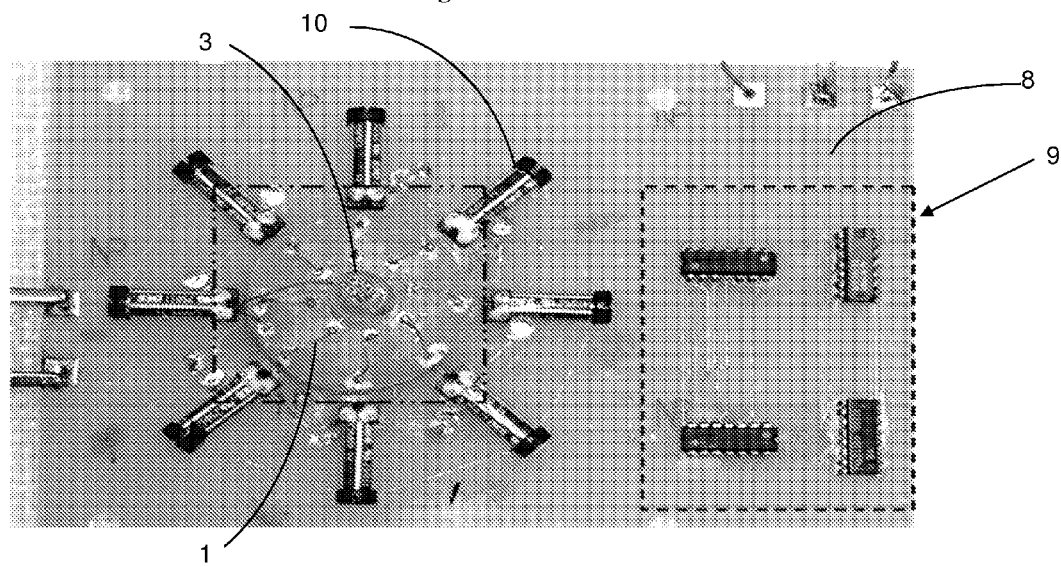
FIG. 2 depicts an image of the assembled 8-electrode device. The Microfabricated device is mounted on a 8-lead PCB board and a switching circuit used for multichannel data recording.

The Microfabricated and assembled 8-electrode device is solder-mounted on an 8-lead printed circuited board (PCB board) (8). The PCB board was fabricated using a standard commercial fabrication process. PCB tracks are electroplated with an approximately 2 μm layer of gold. The board contains pins soldered into contact holes at the end of the leads. The assembled device is shown in FIG. 2. The PCB switchboard was also fabricated with matching holes to those of the lead board. Receptacles are soldered into the holes in the switching board, allowing the device to be plugged and unplugged from the switching board.

The switching circuit (9) consists of a decade ripple counter-SN7490AN; a 3 to 8 decoder, for example a -SA74LS138N; inverters-HD74LS04P; reed relays; LEDs. At the end of each IS scan, a digital high (5V) is output to a selected pin of the digital I/O port of the PGSTSAT equipment. This output is fed to the trigger input of decade counter. Initially, the value of the counter is set to '000' in 3 digit binary representation. The output of the counter is decoded using a 3 to 8 decoder to represent 11111110. This value is inverted using inverters to 00000001. These binary digits are fed to the control terminal of the eight reed relays (10), which are connected to eight working electrodes. The logic '1' in the first position of this value will switch (ON) the first relay. At this stage the input signal from the PGSTAT is routed to that particular working electrode and the impedance is recorded. At the end of the measurement scan, a digital high (5V) is fed to the trigger input of the decade counter. The count increases from 000 to 001, thereby switching the second relay on and hence the second working electrode Impedance is recorded using FRA2 impedance analyzer for each electrode and the process repeats till measurements are recorded at all 8 electrodes. Reed relays (10) were used as switching elements because of their high isolation. LEDS indicate the active channel.

Upon completion of device fabrication, a 5 mm internal diameter, glass cloning cylinder (4) of 500 μl capacity was attached at the center of the electrode array using commercial two-part epoxy to serve as a cell culture well. After the epoxy dried for 10 minutes, DI water is dispensed in the culture well. The device is placed in a 50° C. incubator for 12 hours to allow chemicals to diffuse out of the epoxy into the liquid. The device is washed in acetone, methanol and DI water for 2, 2 and 5 minutes respectively. The assembled device modules (carrier board) being separate from the control board, allowed easy interchange of devices between experiments. An AGILENT™4294A impedance analyzer (5) and a pseudo 4 point probe which facilitates bipolar measurements, in tandem with a CASCADE™ microprobe station was used for impedance measurements. Electrical circuits (6) connect impedance analyzer (5) to test electrodes (1). Measurements were performed from 40 Hz to 100 MHz, with a signal level of 25 mV.

Upon inoculation of the cell suspension on the microfabricated device, the cells (2) will adhere to the glass substrate and proliferate, forming cell layer (7). Since the Au electrodes are fabricated on the surface of the glass substrate, encroachment of the cells on the Au surface causes a change in the impedance between WE and CE.

Example 1

Programming the Frequency Response Analyzer (FRA) for Multichannel Impedance Measurements Impedance spectroscopy was performed over a frequency range of 25 Hz to 1 MHz using the frequency response analyzer (FRA2) module of the PGSTAT 30 potentiostat/Galvanostat. To achieve 8-electrode IS scan; the FRA programming interface is utilized. In the FRA programming utility, a procedure is a particular type of measurement, e.g. a frequency scan from 1 Hz to 10 Hz. A project could be a collection of such procedures as well as other I/O utilities.

For an 8-electrode scan, a new project is created which performs the IS procedure 8 times. At the end of each IS scan, a digital high (5V) is output to a selected pin of the digitial I/O port of the PGSTSAT equipment. This output is fed to the trigger input of the 8-electrode switch circuit, facilitating automatic switching to electrode n+1 upon completion of measurements on electrode n. The instrumentation was set up to acquire data automatically over a period of time using the programming capability of the FRA in PGSTAT. The impedance was recorded in the frequency range between 25 Hz and 1 MHz. A 10 mV amplitude signal was used as the excitation potential.

Cells were inoculated on the 8-electrode device using a cell suspension. After dispensing the cells, the devices were placed inside the incubator for a period of 2 hours, to allow cell attachment and spreading. Experiments performed without this inoculation period did not yield cell growth. After 2 hours, measurements were performed for all 8 electrodes, the device was transported back to the incubator. This procedure was repeated until completion of the experiment.

Figure 3:
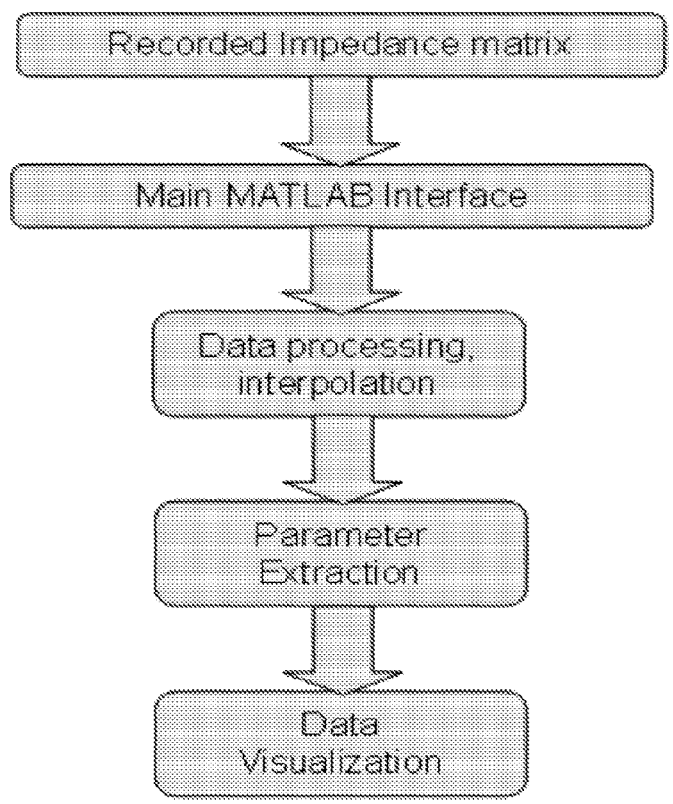
FIG. 3 depicts a flow chart outline of the data processing and analysis algorithm.

An automated GUI-based MATLAB™ routine was developed for automated data analysis and visualization. The GUI facilitates data collection, analysis, parameterization and visualization. An outline of the task flow for the MATLAB™ based GUI is shown in FIG. 3.

Data is imported from the primary AUTOLAB™ directory (source) on the PC into the MATLAB™ directory (destination). The program requires user input in pointing out the source and destination directories, thereby avoiding cross-mining of data and overlapping variable assignments in MATLAB™. The data is then converted into time frames. Each time frame consists of a NX8 matrix, where N is the number of frequency points and 8 is the number of electrodes. Each column of this matrix corresponding to a particular electrode and consists of a complex vector. Each element of this vector is a complex number representing the impedance of a particular electrode at a particular frequency at a particular time. The entire dataset is 5-dimensional. Data is then processed through a "for" loop which extracts the parameters of the complex impedance data for each electrode at any given time instance. The data is then analyzed using computational tools, such as least square data fitting and regression analysis, the model parameters are varied to fit experimental observations. The quality of the fit is then evaluated. This process is repeated by refining the model until a good fit is obtained.

Figure 4:
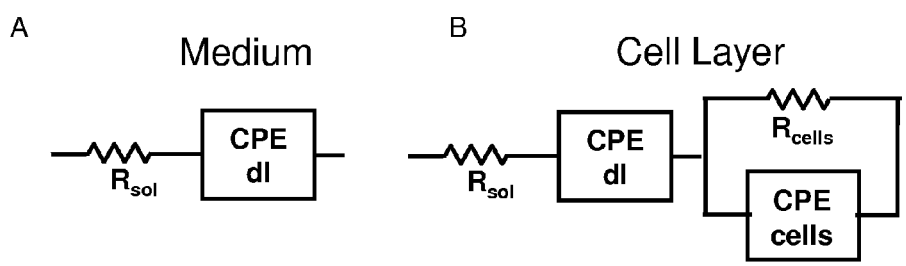
FIGS. 4(*a*) and (*b*) depict circuit models. The ciruits were considered equivalent circuits, used to parameterize medium only (a) and cell layer (b) impedance data.

Several cell-substrate and cell-cell interaction parameters are monitored in tandem using GUI parameter extraction. A four parameter circuit is identified, which represents the impedance of the electrode in the presence of cells. Three MATLAB™ functions are utilized to perform curve fitting and parameter extraction namely, FMINSEARCH, LSQNONLIN and LSQCURVEFIT. The same circuit can be used to model the data in the absence of cells, however, the cell layer parameters will not be well determined. The confidence interval of a parameter can be used to identify the importance of a parameter to the fit. The equivalent circuit used to model the data, seen in shown in FIGS. 4(a) and (b), for (b) presence and (a) absence of cells.

Figure 5:
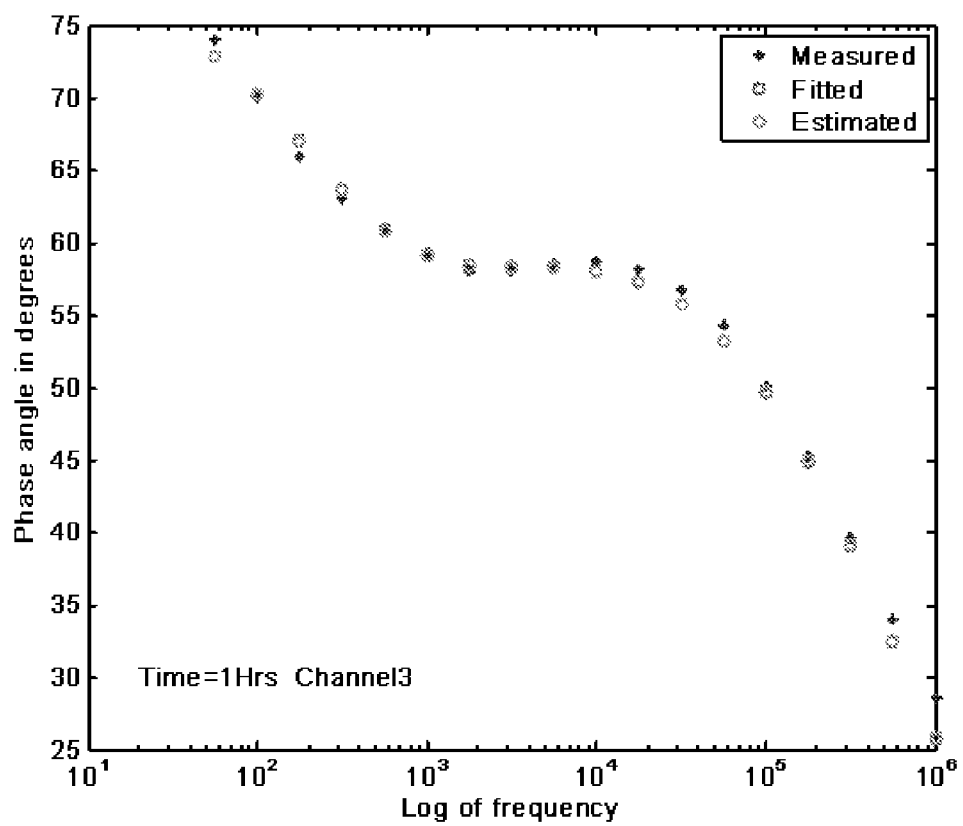
FIG. 5 depicts a graph of the measured, estimated, and fitted data of OvCa429 cell culture.

FIG. 5 is the measured and simulated (using estimated parameters) plot of OvCa429 cell culture impedance. The plot 'Fitted' is simulated with estimated parameters obtained using Fminsearch. The plot 'Estimated' is simulated with parameter estimates obtained using Lsqnonlin. It is observed that the parameter estimates from LSQNONLIN and LSQCURVEFIT are very close to each other. Using two algorithms, though not necessary, allows cross validation and back-up if one function fails to minimize.

Example 2

Effect of Electrode area on Impedance Evaluation of Tissue and Cell Culture

The effect of microelectrode geometry on the impedance response of four analytes was studied using 0.85% potassium chloride (KCl) (conductivity of 14.28 mS/cm), Human umbilical endothelial cells, (HUVEC, Clonetics Corp., San Diego, Calif.), human skin cells, and medical imaging gel (Spectra 360™ Electrode gel). Since capacitance is directly proportional to area, interfacial polarization is an area dependent property. In the case of microelectrodes, this effect can lead to enormous impedances easily reaching the limit of contemporary measurement equipment, particularly at low frequencies. At small electrodes, high current density can lead to heating and other non-linear effects.

HUVECs were cultured in endothelial cell growth medium (EGM; Clonetics Corp.) at 37° C. with 5% $CO_2$, and subcultured at 70% confluency. HUVECs passaged less than six times were used in experiments. Twenty-four hours after inoculating cells in the inventive device, the normal medium was replaced by Hanks' Balanced Salt Solution (HBSS; Mediatech, Inc., Herndon, Va.) without phenol red.

The skin samples (U.S. Cell and Tissue Bank, Ohio) were kept in a freezer until measurements were performed. Shortly before the experiments, sufficient samples were transported in dry ice from the freezer to the experimental setting. Samples were sectioned to ensure full coverage of the electrodes. They were dabbed dry paper and then placed on the Electrode (stratum corneum (SC) side down) and lightly pressed to ensure good contact.

Device Microelectrode Characterization

Figure 6:
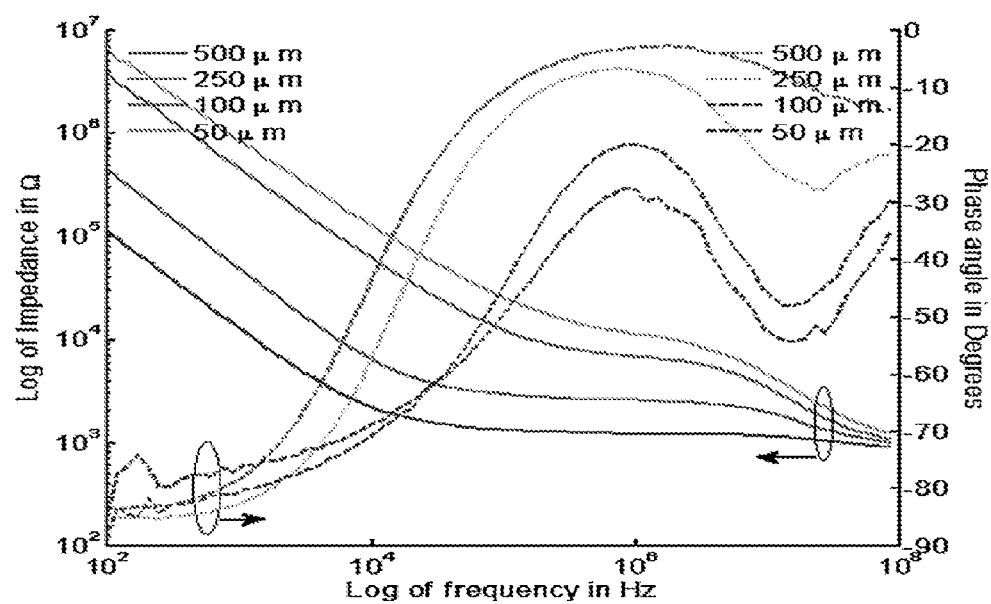
FIG. 6 depicts a Bode diagram of KCl solution in the device using varying electrode areas.

The characteristics of the four electrode sizes—500 μm, 250 μm, 100 μm, and 50 μm—in KCl was determined via a Bode plot, as seen in FIG. 6. The interfacial polarization regime is identified by the low frequency (<10 kHz) power law behavior of impedance magnitude. This slope shifts upwards with a decrease in electrode area due to the inverse relationship between electrode area and interfacial capacitance. At high frequencies (>10 kHz), a second frequency dispersion is observed, arising from the effect of polymer coating used to define the area of electrodes (electrode tips) by lithography and isolate the metallic electrical contact from contributing to the electrochemical impedance. The second dispersion is also visible in the Bode phase plot, where a second phase minima is seen for all electrode sizes except the 500 μm electrode. The absence of second dispersion from the largest area electrode is attributed to the lower interfacial impedance of the larger (500 μm) electrode.

In the measured frequency range, the contribution of coating capacitance can be reduced by either increasing the exposed area of the electrode or by increasing the thickness of the polymer coating, as seen in Table 1. The use of hydrophobic coatings such as SU-8 reduce the drift in the sensor due to water uptake in the polymer. Alternatively, several other approaches can be adopted to increase the interfacial capacitance including electroplating and surface roughening.

TABLE 1

Electrical equivalent parameters of the impedance data for KCl electrolyte.

| Parameter/electrode | 500 μm | 250 μm | 100 μm | 50 μm |
|---|---|---|---|---|
| $R_{sol}$ (Ω) |  | 7.19E2 | 7.78E2 | 7.62E2 |
| $R_{sp}$ (Ω) | 1.33E3 | 2.16E3 | 7.30E3 | 1.36E4 |
| $Y_{dl}$ (S·s$^n$) | 2.02E-8 | 4.61E-9 | 7.76E-10 | 5.36E-10 |
| $n_{dl}$ | 0.94 | 0.95 | 0.89 | 0.86 |
| $Y_{coat}$ (S·s$^n$) | 4.50E-9 | 4.43E-10 | 4.20E-11 | 4.71E-11 |
| $n_{coat}$ | 0.57 | 0.77 | 0.87 | 0.85 |

The parameterization of spreading resistance into spreading and solution resistances was necessary to achieve a good fit. For planer electrodes the value of resistance commonly referred to as the spreading resistance is determined by the area of the metal in contact with the electrolyte. In the present scenario, at lower frequencies, the solution resistance is due to the exposed area of the electrode (lithographically defined) . However, at higher frequencies the AC signal begins to permeate through the coated area of the electrode at approximately 20 to 60 µF/cm² of (double layer) capacitance for every cm² of electrode area for metal in an electrolyte.

Figure 7:
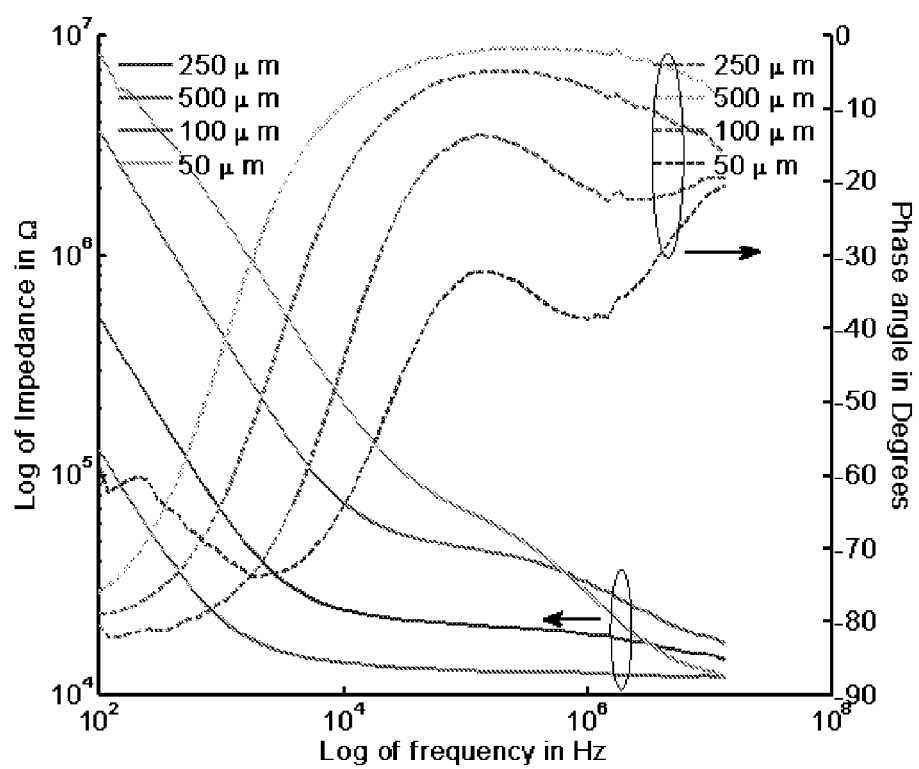
FIG. 7 depicts a Bode diagram of spectra 360 electrode gel in the device using varying electrode areas.

The impedances of the four electrode sizes measured by using Spectra™ analyte are similar to KCL impedances, as summarized in Table 2. One departure from the expected behavior is the impedance magnitude of 50 µm electrode, which exhibited a sharper coating dispersion (steep slope) in comparison with the other electrodes, and attributed to the higher current density effects. The inverse relationship between impedance magnitude and electrode area seen in FIG. 7. The resistance of Spectra™ is lower than the KCl, as noted from the extrapolation of plateau region on to the y-axis of the Bode plot. Consequently, the coating dispersion occurs much earlier in the frequency scale for Spectra™. This indicates excellent conductivity of this gel, comparable to the liquid electrolyte.

TABLE 2

Electrical equivalent parameters of the impedance data for Spectra ™ electrode gel.

| Parameter/electrode | 500 µm | 250 µm | 100 µm | 50 µm |
|---|---|---|---|---|
| $R_{sp}$ (Ω) | 6.22E3 | 6.96E3 | 1.53E4 | 2.13E4 |
| $Y_{dl}$ (S·s$^n$) | 1.05E-7 | 3.13E-7 | 5.68E-8 | 7.98E-8 |
| $n_{dl}$ | 7.43E-1 | 7.41E-1 | 6.89E-1 | 6.70E-1 |
| $Y_{coat}$ (S·s$^n$) | 4.78E-12 | 1.16E-6 | 2.95E-13 | 2.09E-13 |
| $n_{coat}$ | 9.00E-1 | 1.94E-1 | 1.00 | 1.00 |

Example 3

HUVEC Cell Impedance

Figure 8:
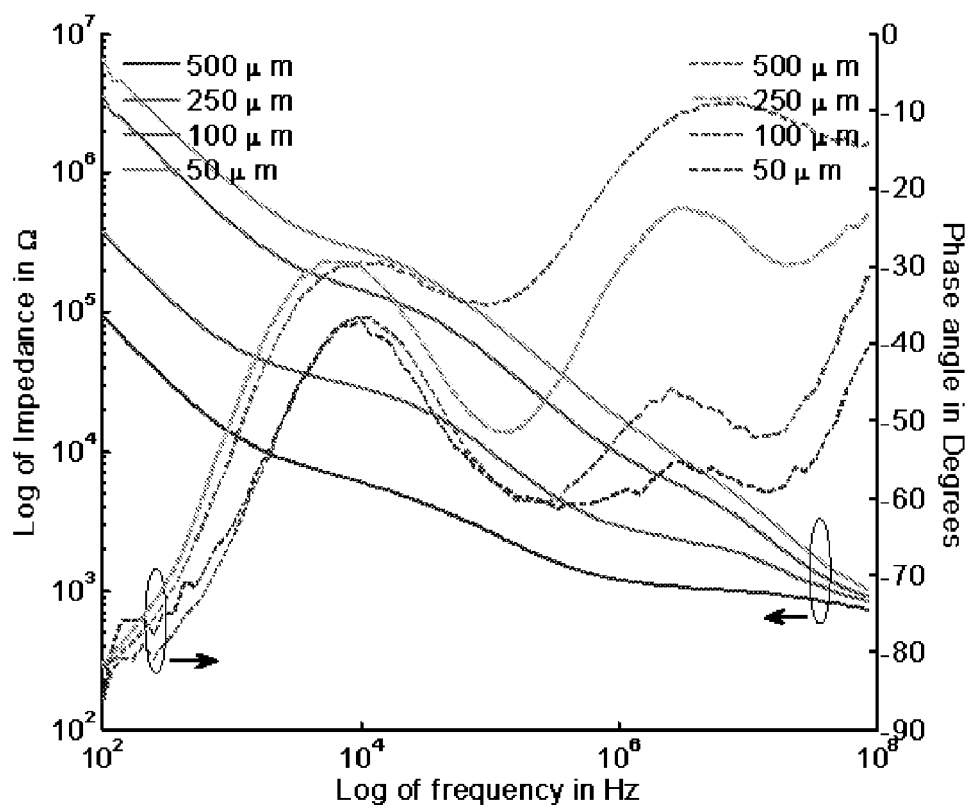
FIG. 8 depicts a Bode diagram of HUVEC in in the device using varying electrode areas. Three phase minimas are observed due double layer, cells and coating in that order

The HUVEC cells form a confluent adherent layer on the electrode. A mid-frequency (approximately 10 kHz) dispersion attributed to the cell layer is observed in the Bode diagram of HUVEC, seen in FIG. 8. The impedance of an electrode-coating-electrolyte system was modified by cellular growth of a confluent cell layer. The sequence in which dispersions caused by the double layer, coating and cell CPE appear is dependent upon the penetration depth of the AC signal and hence the magnitudes of these CPE's. At even higher frequencies (approximately 50 KHz), the AC signal can penetrate the cell layer adjacent to the electrode surface. At the higher frequencies (approximately 1 MHz), the coating impedance becomes comparable to the series combination of double layer and cell layer capacitances; hence AC passes indiscriminately from all areas of the electrode. At this point the cell constant is ill defined, unless measurements is recorded at high enough frequencies (>10 MHz) where a resistance plateau can be attained and new cell constants can be defined.

Figure 9:
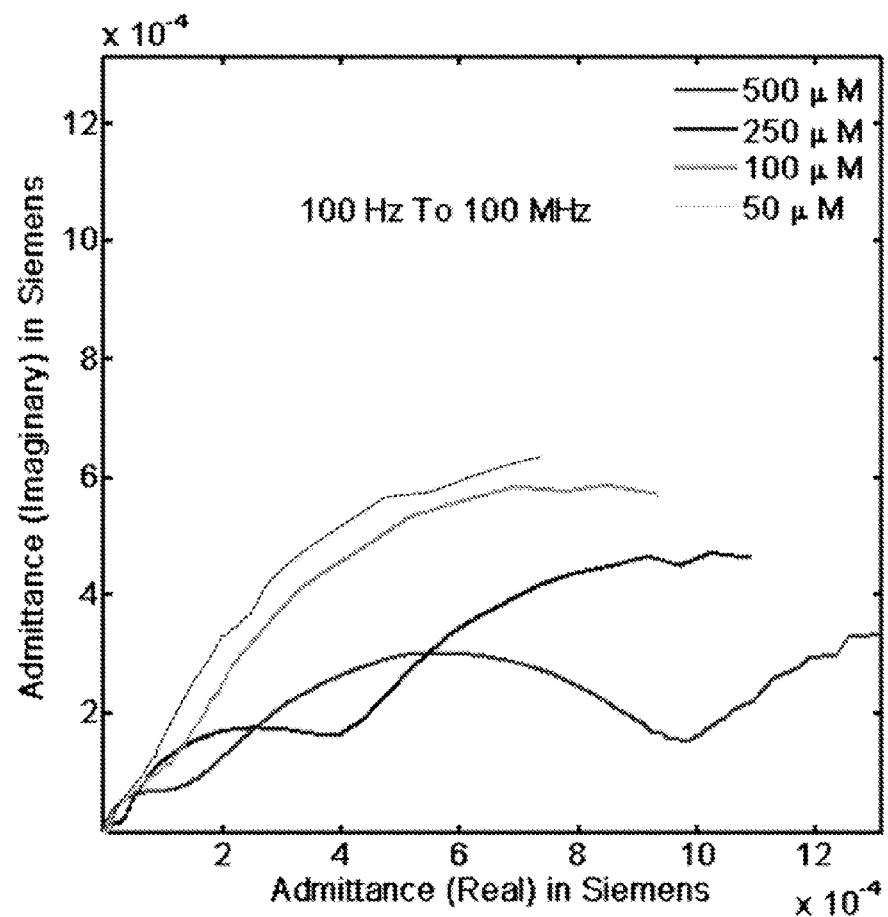
FIG. 9 depicts a complex admittance plot of HUVEC in the device using varying electrode areas.

The admittance spectra of HUVEC culture was determined for four different electrodes of varying geometry, seen in FIG. 9. The three dispersions can be clearly seen in 250 and 500 µm electrodes, while it is less defined in the other two electrode sizes. It is noteworthy that the separation of semi-circles in the admittance plane is in accordance with the magnitude of the phase minima. Larger electrode size leads to lower phase minima and well separated semi-circles in the complex admittance plane.

Figure 10:
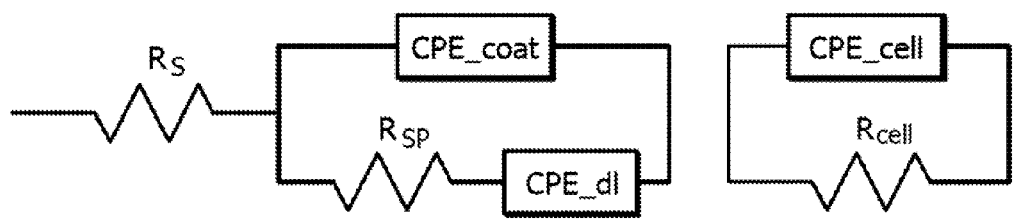
FIG. 10 depicts a circuit diagram used to model the impedance response of HUVECs cultured on microelectrode devices. $R_s$ is solution resistance, $R_{sp}$ is the spreading resistance, CPE_dl is the double layer constant phase element (CPE), CPE_coat is the coating CPE, CPE_cell is the cell CPE, and $R_{cell}$ is the cell layer resistance.

Table 3 lists the extracted parameters of HUVEC by equivalent circuit fitting, using the circuit in FIG. 10. The cellular parameters are distinguished by the value of constant phase element. The cell layer resistance is well above the value of solution resistance due to the high resistance of the cell layer. Besides contributing an additional R-CPE element, the cell layers considerably alter the interfacial polarization due to redistribution of ionic charge in the near vicinity of the electrode.

TABLE 3

Electrical equivalent parameters of the impedance data for HUVEC.

| Parameter/electrode | 500 µm | 250 µm | 100 µm | 50 µm |
|---|---|---|---|---|
| $R_{sol}$ (Ω) | 5.91E2 | 6.78E2 | 6.89E2 | 5.80E2 |
| $R_{sp}$ (Ω) | 3.53E2 | 1.42E3 | 3.61E3 | 4.07E3 |
| $Y_{dl}$ (S·s$^n$) | 2.19E-8 | 5.49E-9 | 6.52E-10 | 4.04E-10 |
| $n_{dl}$ | 0.96 | 0.95 | 0.94 | 0.91 |
| $Y_{coat}$ (S·s$^n$) | 2.24E-11 | 5.18E-11 | 2.45E-11 | 3.82E-11 |
| $n_{coat}$ | 0.95 | 0.90 | 0.93 | 0.91 |
| $R_{cell}$ (Ω) | 6.72E3 | 3.22E4 | 1.39E5 | 2.83E5 |
| $Y_{cell}$ (S·s$^n$) | 4.53E-8 | 1.94E-9 | 3.01E-10 | 3.03E-10 |
| $n_{cell}$ | 0.69 | 0.81 | 0.83 | 0.79 |

Example 4

OvCa Cell Impedance

Ovarian cancer line OvCa429 were grown in M199 and MCDB 105 (1:1) (Sigma, St Louis, Mo.) supplemented with 10% fetal calf serum (Sigma), 2 mM L-glutamine, 100 units ml-1 penicillin and 100 µgml-1 streptomycin under 5% CO2, and 37 .C high-humidity atmosphere. The cell culture medium was changed every 2-3 days, depending on the rate of cell growth. Cells were sub-cultured using 1× trypsin solution directly on the multielectrode device Impedance data were taken at room temperature of about 22° C. After each recording the cells were placed back in to the incubator. The cell culture medium was not changed throughout the course of the experiment. Impedance measurements were recorded on two separate devices (control and variable) beginning at approximately 80% confluence of the OvCa culture. After 5 h of recording measurements at an interval of approximately 1 h, 20 µl of trypsin was added to the cell culture medium of variable. Trypsin was not added to the control. The impedance was recorded under room conditions and the devices were placed back in the incubator after each measurement frame.

The CPE is used in IS to describe several scenarios such as surface roughness of the electrodes, non-uniform current distribution, distribution of reaction rates, among other processes. The impedance of cell culture medium (HBSS) was monitored for 160 hours to serve as a control. OvCa429 were inoculated at 10⁶ cells/cm² and allowed to stabilize for 2 hours. Thereafter, impedance was monitored for 116 hours with a total of 15 measurements were obtained. The cell culture medium was replaced by 0.25% Trypsin-EDTA at 68 hours of cell culture.

The phase angle of impedance of control, comprising cell culture medium only (column A) and the OvCa429 culture (column B), was mapped in 3 dimensions over the course of approximately 70 h, seen in FIGS. 11(a)-(d) and FIGS. 12(a)-(d). The analysis of this dataset can be either shape-based (area under the curve, surface normalization) or parametric (equivalent circuit modeling). Equivalent circuit analysis is performed on the OvCa429 impedance dataset to determine the interfacial and cell-layer parameters. Parameter estimation by equivalent circuit modeling provides specific data pertaining to the interaction of cells with the substrate and with each other in a quantified manner.

Figure 11:
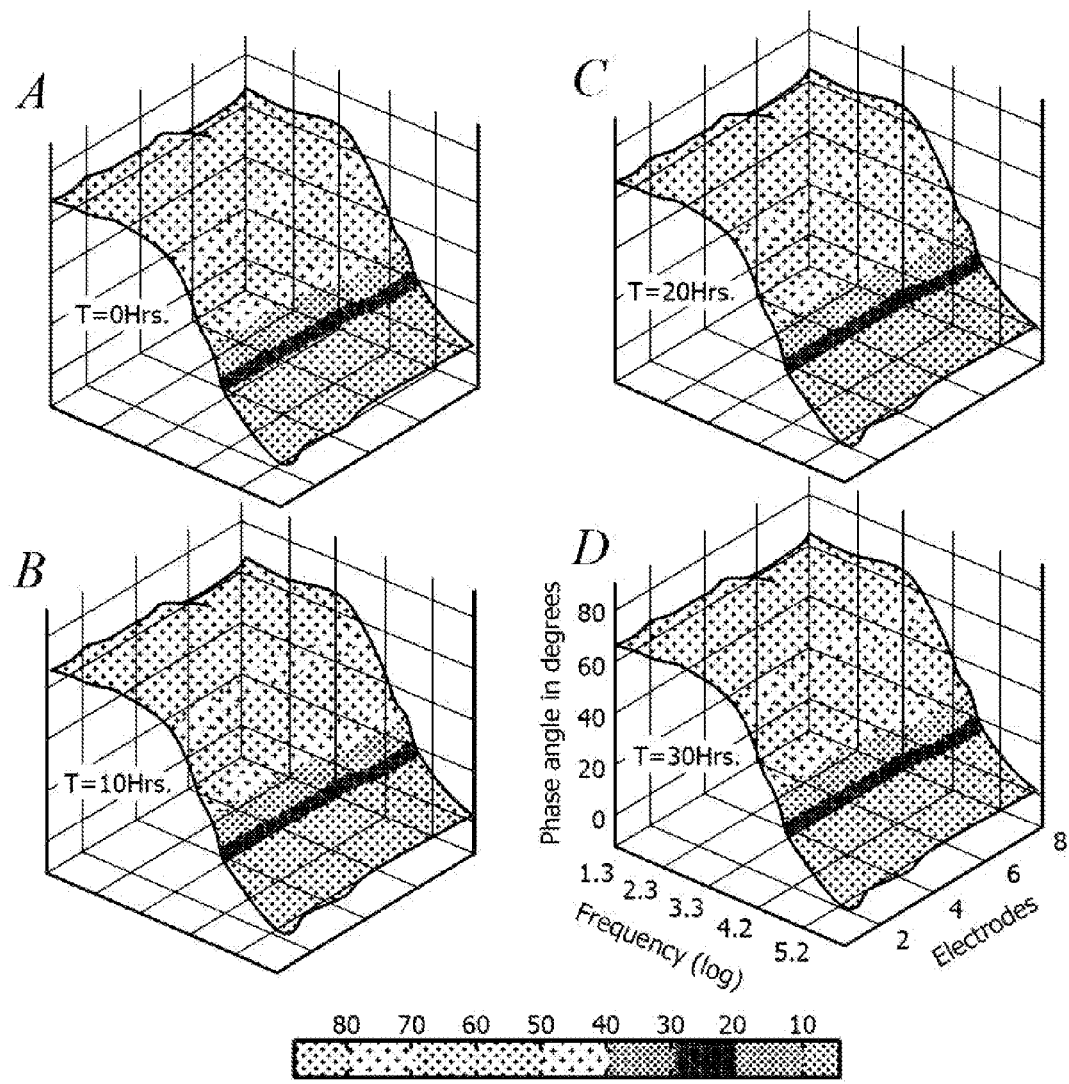
FIG. 11(*a*)-(*d*) are 3 dimensional phase angle map graphs of the adhesion and proliferation of OvCa429 cells. The graphs were taken at varying times for cell culture medium, which serves as the control. All of the above plots have a common X, Y and Z scale which is only shown in the last set of plots (T=70 h). The X-axis is the logarithm of measured frequency ranging from 1.3 to 6, the Y-axis is the number of electrodes ranging from 1 to 8 for the eight-electrode array, and the Z-axis is the phase angle of impedance in degrees ranging from −10. to 90. The sign of the actual phase angle has been reversed in the 3D plot for graphing convenience. The annotation T=n Hrs in the plots indicates time in hours elapsed since the inoculation of cells in the electrode array.
Figure 12:
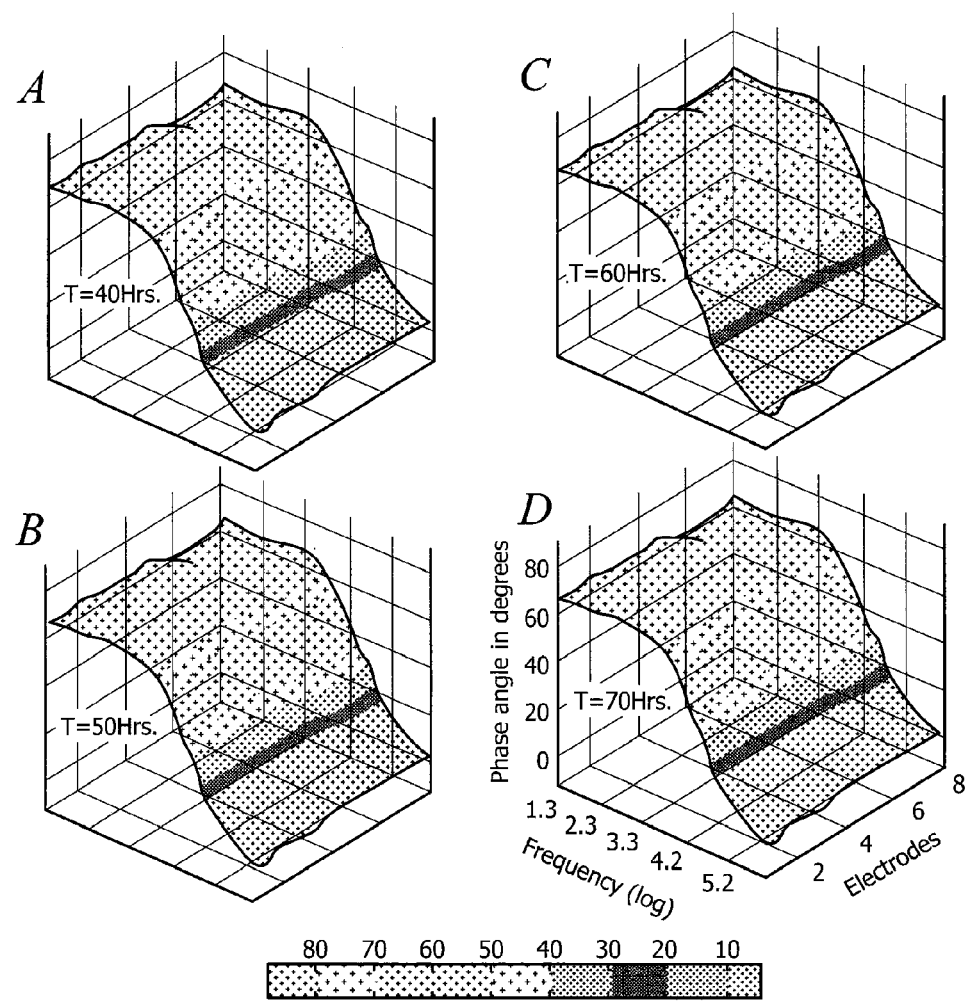
FIG. 12(*a*)-(*d*) are 3 dimensional phase angle map graphs of the adhesion and proliferation of OvCa429 cells. The graphs were taken at varying times for cell culture medium, which serves as the control. All of the above plots have a common X, Y and Z scale which is only shown in the last set of plots (T=70 h). The X-axis is the logarithm of measured frequency ranging from 1.3 to 6, the Y-axis is the number of electrodes ranging from 1 to 8 for the eight-electrode array, and the Z-axis is the phase angle of impedance in degrees ranging from −10. to 90. The sign of the actual phase angle has been reversed in the 3D plot for graphing convenience. The annotation T=n Hrs in the plots indicates time in hours elapsed since the inoculation of cells in the electrode array.
Figure 13:
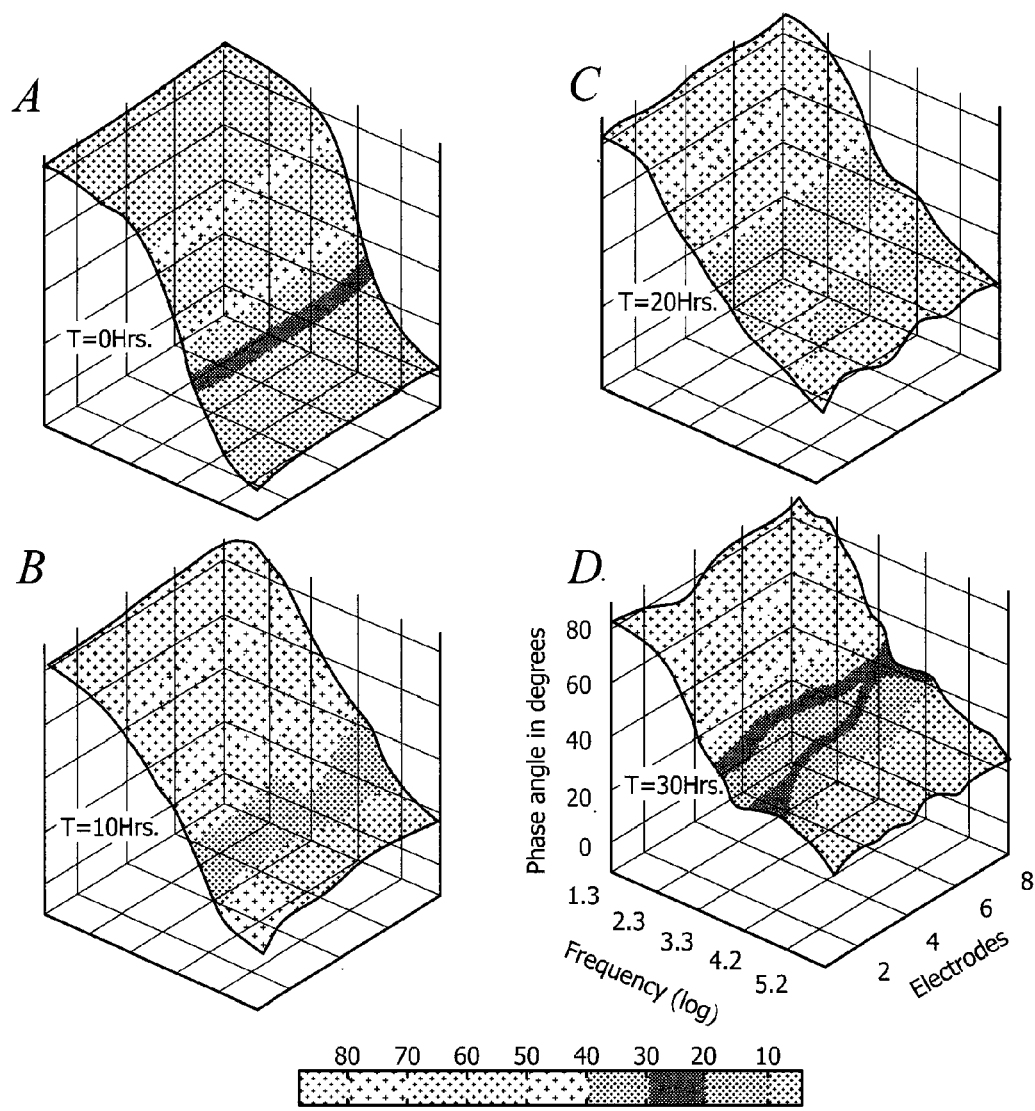
FIGS. 13(*a*)-(*d*) are 3 dimensional phase angle map graphs of the adhesion and proliferation of OvCa429 cells. The graphs were taken at varying times for cell culture medium containing 106 cells cm-2 of OvCa429. All of the above plots have a common X, Y and Z scale which is only shown in the last set of plots (T=70 h). The X-axis is the logarithm of measured frequency ranging from 1.3 to 6, the Y-axis is the number of electrodes ranging from 1 to 8 for the eight-electrode array, and the Z-axis is the phase angle of impedance in degrees ranging from −10. to 90. . The sign of the actual phase angle has been reversed in the 3D plot for graphing convenience. The annotation T=n Hrs in the plots indicates time in hours elapsed since the inoculation of cells in the electrode array.

In the initial stages of the cell culture, when the cells are in the suspended state, the phase angle shapes of the control, seen in FIG. 11(a), and OvCa429, seen in FIG. 13(a), are similar. As the cells adhere and proliferate the shape of the phase angle shape of the OvCa429 culture is markedly different from the control, as seen in FIGS. 11(b)-(d), 12(a)-(d), 13(b)-(d), and 14(a)-(d). This is due to the fact that cells, during adhesion and spreading are in intimate contact with the substrate, which results in a change of impedance.

Figure 14:
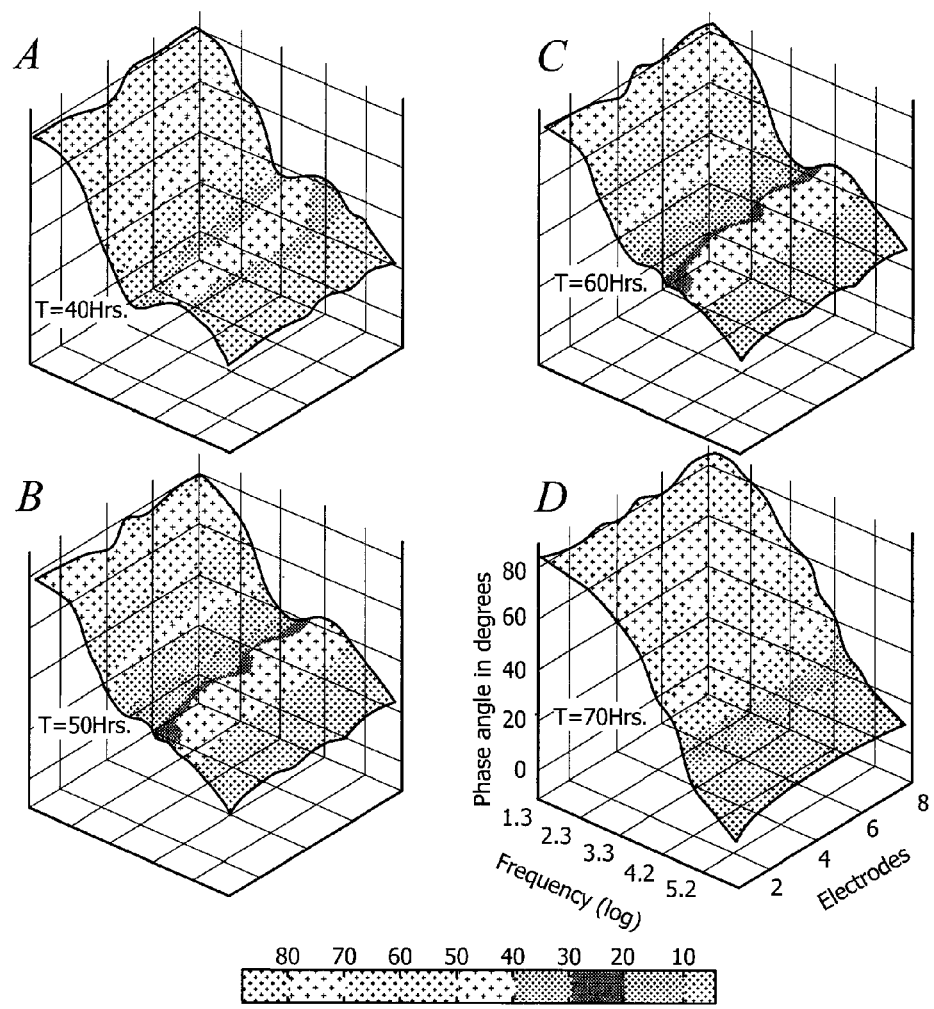
FIGS. 14(*a*)-(*d*) are 3 dimensional phase angle map graphs of the adhesion and proliferation of OvCa429 cells. The graphs were taken at varying times for cell culture medium containing 106 cells cm-2 of OvCa429. All of the above plots have a common X, Y and Z scale which is only shown in the last set of plots (T=70 h). The X-axis is the logarithm of measured frequency ranging from 1.3 to 6, the Y-axis is the number of electrodes ranging from 1 to 8 for the eight-electrode array, and the Z-axis is the phase angle of impedance in degrees ranging from −10. to 90. . The sign of the actual phase angle has been reversed in the 3D plot for graphing convenience. The annotation T=n Hrs in the plots indicates time in hours elapsed since the inoculation of cells in the electrode array
Figure 15:
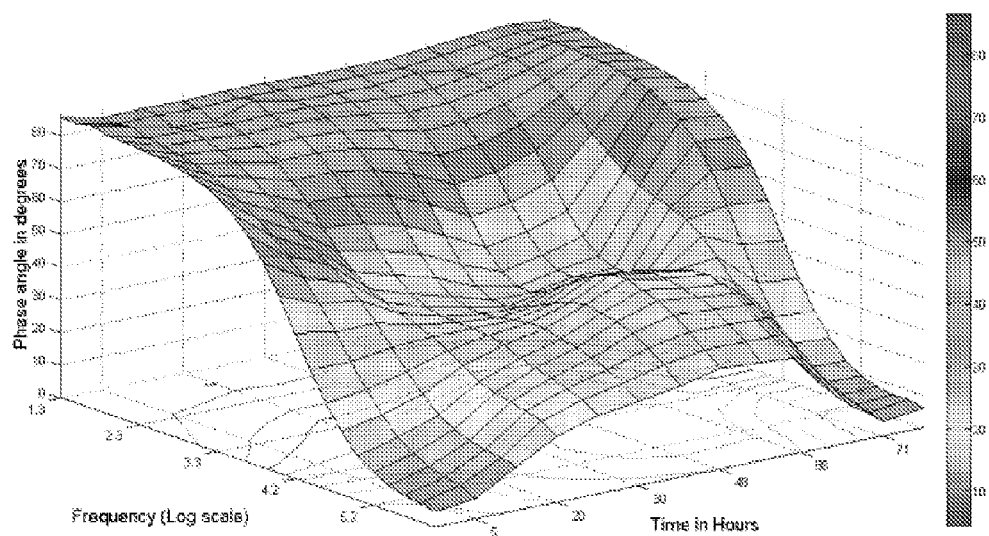
FIG. 15 is a surface plot of phase angle as a function of frequency and time. Changes in the phase angle of electrode designated 1 in the multielectrode array with the progression of culture time. A second phase minimum is seen to develop as a consequence of cell adhesion and proliferation. The phase angle is restored back to the pre-culture level upon cell detachment. The sign of the phase angle has been reversed for graphing convenience.

Beyond T=50 h, seen in FIGS. 14(c) and (d), the cells gradually begin to detach from the substrate and lose viability due to lack of nutrients in the culture medium, which was not replenished through the course of the experiment. As a consequence of cell detachment, the phase angle at 70 h resembles that of the control, as seen in FIGS. 12(c) and (d). This confirms that the changes in the shape of the phase angle curve are caused by the morphological changes in the cell culture. FIG. 15 shows the changes in the phase angle of impedance as a result of cell adhesion and proliferation for one electrode (electrode 1) of the multielectrode array. With the progression of culture time a second phase minimum is seen to develop in the frequency range between approximately 10 kHz and 300 kHz. This feature is absent in the control, from which it can be inferred that it is due to the contribution of cells' adhesion to the substrate.

An adaptive MATLAB™ algorithm was used to parameterize the impedance due to cell-substrate and cell-cell interactions. The lower frequencies reflect the cell-substrate interactions, whereas the higher frequencies reflect the cell-layer properties. The thickness of the electrical double layer is a few nm. The closest approach of the cells to the substrate is a few tens of nm's. Consequently, cell coverage and motility are reflected in the impedance data in the lower frequency range (<1 KHz), whereas the cell layer capacitance and tight junctional resistance are reflected at higher frequencies. This is due to the penetration depth of the AC signal, which at higher frequencies can surpass the blocking effect of the double layer capacitance.

Figure 16A:
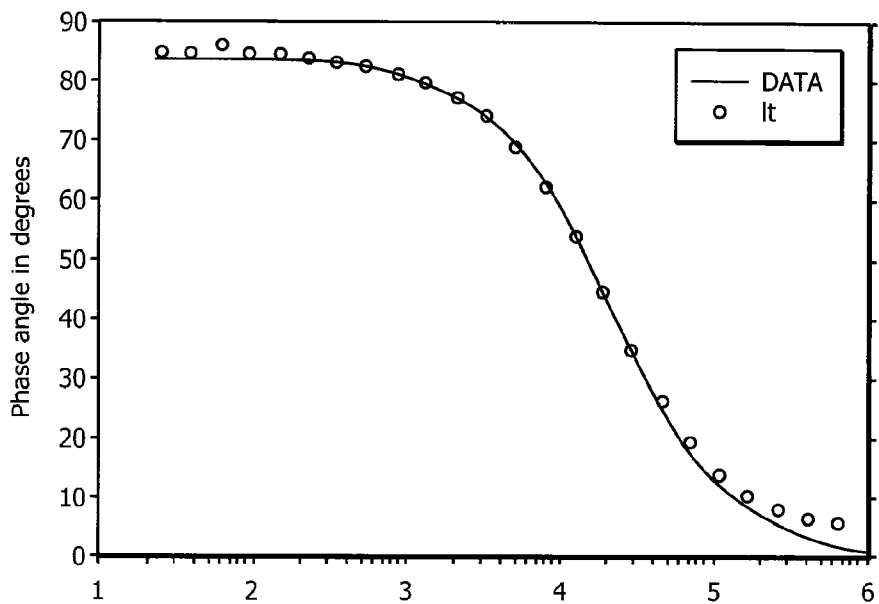
FIGS. 16(*a*) and (*b*) depict phase angle as a function of logarithm of frequency of (a) control cell culture medium fitted with an equivalent circuit shown in FIG. 16(*a*) and (*b*) OvCa429 culture fitted with an equivalent circuit shown in FIG. 16(*b*).

FIG. 16(a) is the recorded impedance of control (culture medium only) of a single electrode (electrode 1) of the multielectrode array. The phase angle progresses from approximately −80° at low frequencies to approximately −5° at high frequencies. This behavior is mimicked by an electrical circuit comprising a resistor and capacitor in series. The resistive parameter models the effect of ionic resistance of the electrolyte and the capacitive element accounts for the space charge distribution due to the accumulation of charges at interface, known as the double-layer capacitance. In most electrochemical systems, the pure capacitive element is rarely seen; a more realistic representative element of the interfacial space charge is the constant phase element (CPE).

At the electrode-electrolyte interface, the excessive charge of the metal leads to a build-up of opposing charge in the electrolyte. This space charge region gives rise to a capacitor-like effect in the electrochemical impedance domain, represented by the CPE. The impedance of a capacitor is expressed as $(j\omega C)^{-1}$, where C is the capacitance and $\omega$ is the frequency in radians. The impedance of the CPE is expressed as $Q(j\omega)^{-n}$, where Q is the magnitude of the CPE, n is a parameter whose value ranges from 0 to 1. The value of n=1 corresponds to a pure capacitor and n=0 corresponds to a pure resistor. The unit of Q is (S s).

A resistor-CPE series combination is a good approximation of the impedance behavior of electrode-electrolyte systems comprising gold electrodes, which act as blocking electrodes, exchanging little charge with the electrolyte. The impedance in the absence of cells is simply the interfacial impedance in series with the ionic solution conductivity. The recorded phase angle of control and the equivalent circuit representation, shown in FIG. 16(a), are in good agreement, thereby validating the model.

Figure 16B:
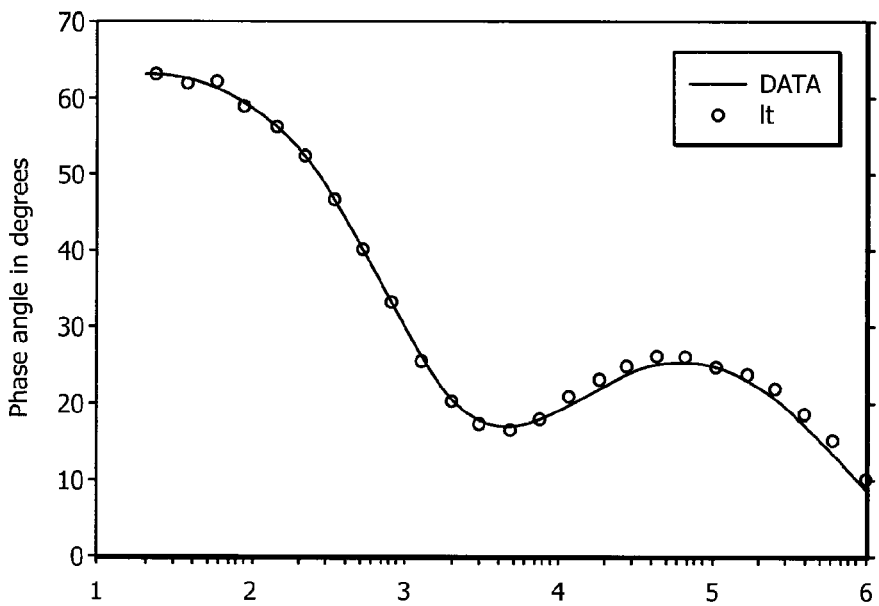

Anchorage-dependent cells rely on substrate contact to proliferate. They form intimate contact with the substrate, a process called adhesion, which alters the electrochemical impedance. The impedance-probing signal has an additional layer to overcome before reaching the solution resistance at higher frequencies. Cell layers contain both capacitive as well as resistive elements. In a two electrode system, the cell layer impedance is in series with the interfacial impedance. The circuit used to fit the electrode-cell system data consists of a series combination of resistance and CPE, in series with a parallel combination of resistance and CPE. The capacitive effect is due to the cell membranes which are insulating and the resistive effect is due to the cytoplasm which is ionic. Additionally, the cell-cell junctions have a finite resistance and contribute to the overall impedance. The equivalent circuit that represents the impedance of the electrode-cell-layer-electrolyte system is shown in FIG. 18(b). In addition to the interfacial elements shown in the circuit of FIG. 18(a), FIG. 16(b) includes a parallel combination of the resistor and CPE to represent cell-layer effects. FIG. 16(b) indicates a good fit between the recorded phase angle of the cell-adhered substrate and the equivalent circuit of FIG. 16(b).

In order to affirm the utility of impedance mapping for tracking physiological changes, the effect of trypsin on the confluent cell culture was analyzed. Equal densities of OvCa429 cells (106 cells cm-2) were seeded on to two separate electrode arrays and incubated under the same set of conditions until 80% confluence (approximately 40 h post-inoculation). One served as a control and the other was used to monitor the effect of trypsin on the confluent cell culture, by adding 20 µl of trypsin to the cell culture medium. Trypsin was added after 5 h of monitoring the impedances of the confluent control and variant (trypsinization) cultures. FIG. 6 is the phase angle mapping of control and trypsinized cultures monitored over a period of 18 h.

Figure 19:
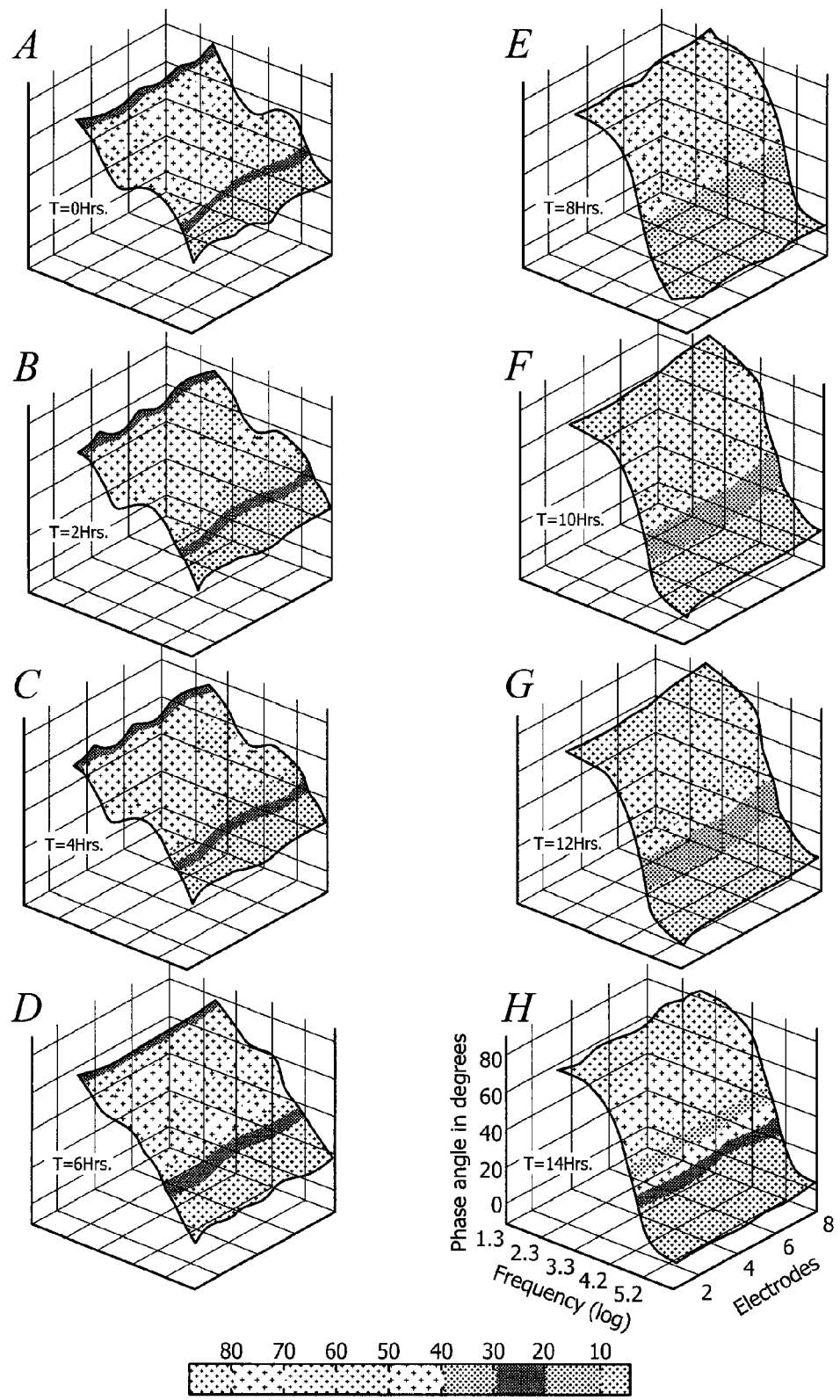
FIGS. 19(*a*)-(*h*) depict the effect of trypsinization on the confluent cell culture monitored by phase angle mapping. OvCa429 cell culture to which 20 µl of trypsin was added.
Figure 20:
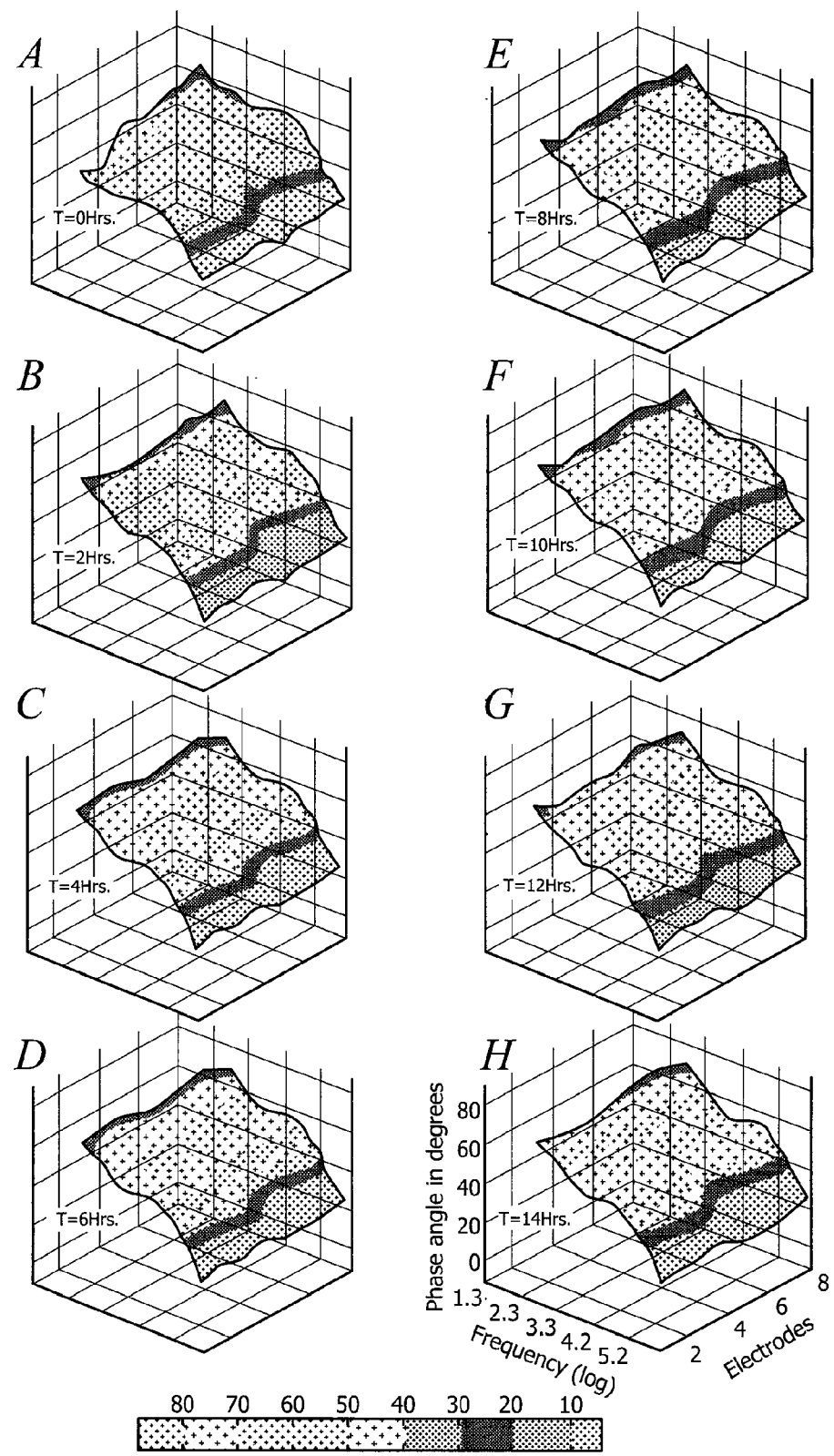
FIGS. 20(*a*)-(*h*) depict the effect of trypsinization on the confluent cell culture monitored by phase angle mapping. The graphs show control samples of confluent OvCa429 cell culture to which nothing was added

After addition of trypsin to the OvCa429 culture, with a growth phased depicted in FIGS. 19(a)-(c), the phase angle shape, seen in FIG. 19 (d)-(h), displays significant change and transition toward the shape which is representative of the absence of cells, seen in FIG. 17(a), and differs significantly from a control culture of cells without trypsinization, seen in FIGS. 20(a)-(h). Therefore, trypsin has detached the cells from the substrate as expected. Further monitoring of control and trypsinized culture did not indicate significant changes.

Figure 21:
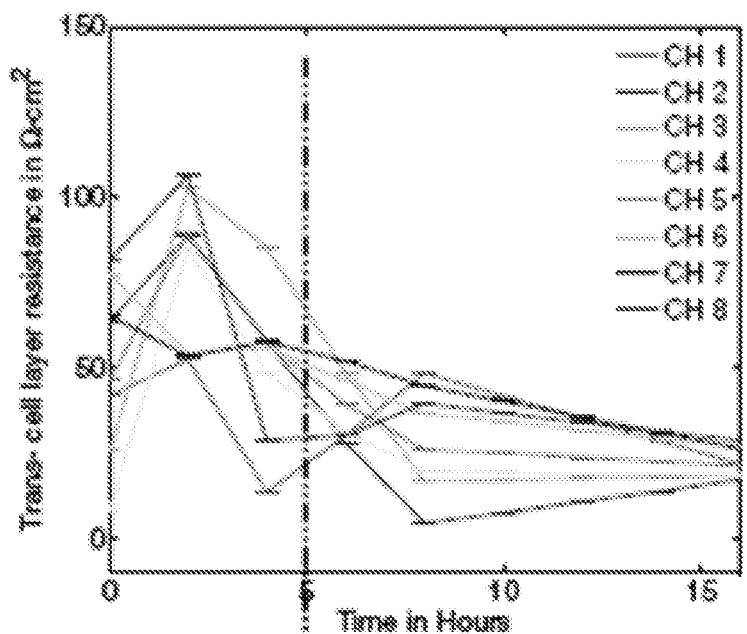
FIG. 21 depicts a graph of cell-layer resistance of control. The horizontal lines indicate the time instance at which trypsin was added to the cell culture. The cell-layer parameters disappear from the electrochemical model upon trypsinization, indicating cell detachment.
Figure 22:
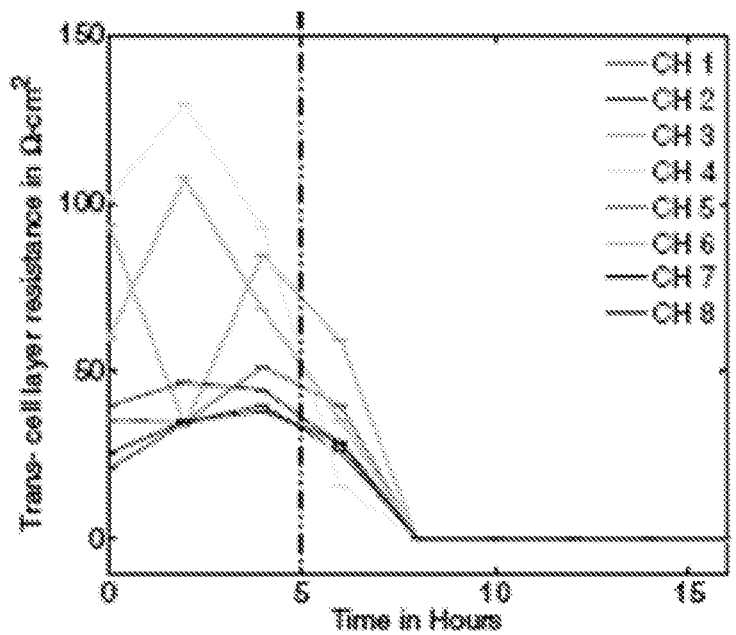
FIG. 22 depicts a graph of cell-layer resistance of the trypsinized culture (trypsin added after 5 h of monitoring). The horizontal lines indicate the time instance at which trypsin was added to the cell culture. The cell-layer parameters disappear from the electrochemical model upon trypsinization, indicating cell detachment.
Figure 23:
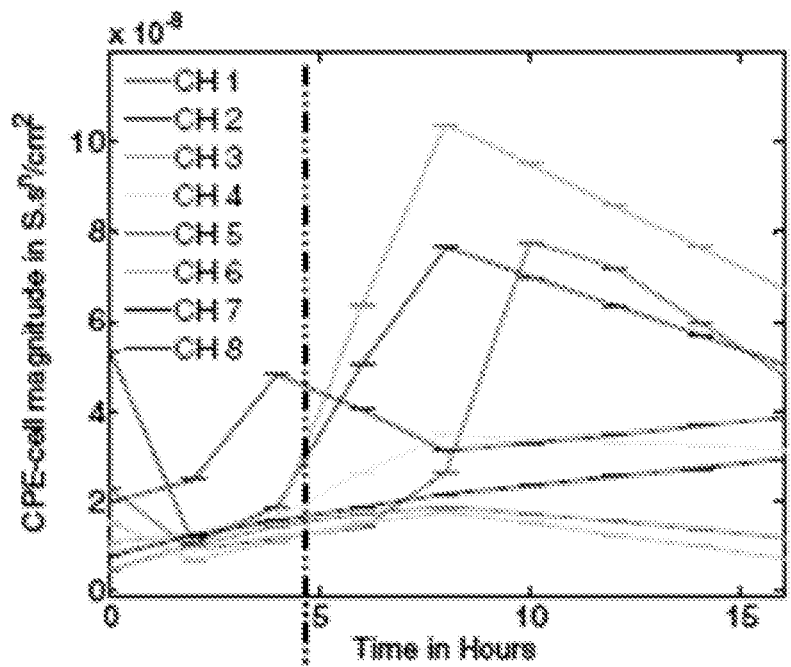
FIG. 23 depicts a graph of cell-layer CPE magnitude of control. The horizontal lines indicate the time instance at which trypsin was added to the cell culture. The cell-layer parameters disappear from the electrochemical model upon trypsinization, indicating cell detachment.

The MATLAB™ algorithm was used to extract the parameters of the impedance dataset using the two model fitting system to parameterize the impedance response of cell culture medium alone and cells in culture medium. The spreading resistance of electrodes in the presence of cells as a function of time was plotted, seen in FIG. 21, showing a decreasing trend with the progression of cell culture. This may be due to the availability of additional ions from the ionic activity of the cells. The spreading resistance shows a slight increase near confluence followed by a drop in resistance during detachment, which appears to be a function of proximity of cells to the substrate and gap junction. The spreading decreases in the time duration (20-60 hours) when the cells are in close proximity to the electrodes, but not tightly bound to each other. After trypsinization of the cell culture at 5 h the observation period causes a decrease in the cell-layer resistance, seen in FIG. 22, and CPE, seen in FIG. 23, followed by the elimination of these parameters from the model representing the data. Hence this could be a suitable way to study cytotoxicity.

Cell Layer (Tight-Junctional) Resistance

Cell layer resistance (tight junctional) was analyzed as a function of culture time (data not shown). The tight-junctional resistance increases as with culture time until confluence, and decreases thereafter until detachment at around 50 hours post inoculation. This is consistent with known times of detachment of OvCa429 cells when left in the same culture medium since inoculation. The nutrients in the medium are consumed and the medium turns acidic. Cells begin to detach and die. Upon trypsination, the junctional resistance vanishes.

Cell Layer CPE-Magnitude

Figure 24:
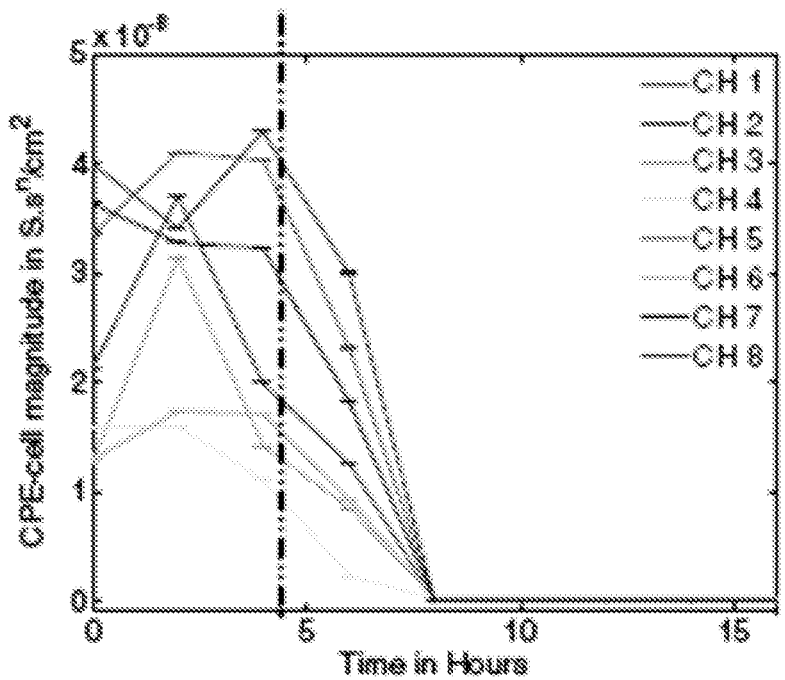
FIG. 24 depicts a graph of cell-layer CPE magnitude of the tripsnized culture. The horizontal lines indicate the time instance at which trypsin was added to the cell culture. The cell-layer parameters disappear from the electrochemical model upon trypsinization, indicating cell detachment.

The cell layer capacitance displays an increasing trend when plotted as a function of time, as seen in FIG. 24. In the early stages of cell culture (approximately 5 hours) this parameter has lowest confidence interval, and is not an important parameter in modeling impedance data corresponding to that time period as the cell layer is only beginning to form at this stage. Beyond 5 hours, this parameter has a high confidence interval, and becomes an important parameter in the overall model. The CPE-magnitude shows a general increasing trend until tripsination. The CPE-cell magnitude values of electrodes 1, 8 and 7 are lower than those of the other electrodes, indicating a cluster of loosely bound cells (cell cluster), as electrodes 1, 8 and 7 are adjacent to each other forming a triangular sector. Over time, the cell layer reaches the same level of confluence as other parts of the culture space (Time=49 hours). This indicates that the device is capable of resolving non-uniform cell density distribution across the 2 dimensional culture space.

The penetration depth of the ac signal increases with frequency. Consequently, the information available from spectroscopy data is dependent on the frequency range of investigation. In the electrode-cells-electrolyte system, the lower frequencies reflect the cell-substrate interactions (interfacial), whereas the higher frequencies reflect the cell-layer (morphological) properties.

The spreading resistance parameter represents the opposition to the flow of current from the working to the counter electrode. Since the field lines spread in planar electrodes, rather than remaining confined to the geometry of the electrodes (e.g. ideal parallel plate electrodes), it is referred to as spreading resistance. In the cell culture well, the spreading resistance depends on the available ionic charges as well as physical obstruction to the flow of these charges. The available ionic charge depends on the concentration of ionic species at any given point, which is dependent upon the rate of consumption and metabolism by the cells. The physical obstruction to the flow of the ions stems from the close approach of anchorage-dependent cells to the substrate, whereby the ions have to circumvent the cells at low frequencies to travel to the counter electrode. Thus, the spreading resistance is an indicator of cell metabolism and cell-substrate interaction. Similarly, the double-layer CPE is also a function of the two factors mentioned above, although it is likely (based on the cell-substrate separation) to be influenced more by the change in the diffusion layer capacitance due to the presence of the cell membrane.

The resistance and the CPE parameters representing the cell layers display a clear correlation between cell-layer formation, confluence and detachment. The cell junction resistance is dependent upon the cell-cell gap, also referred to as the gap junctional resistance. The higher this parameter, the closer the cells are. It is highest at confluence which is consistent with optical observations. Beyond confluence, the layer begins to detach due to non-supply of fresh nutrients and upon trypsinization. The cell-layer-related parameters are not required in the fitting of data when the cells are suspended and when detached by trypsinization, as evident from the shape of the phase angle curves.

Figure 25:
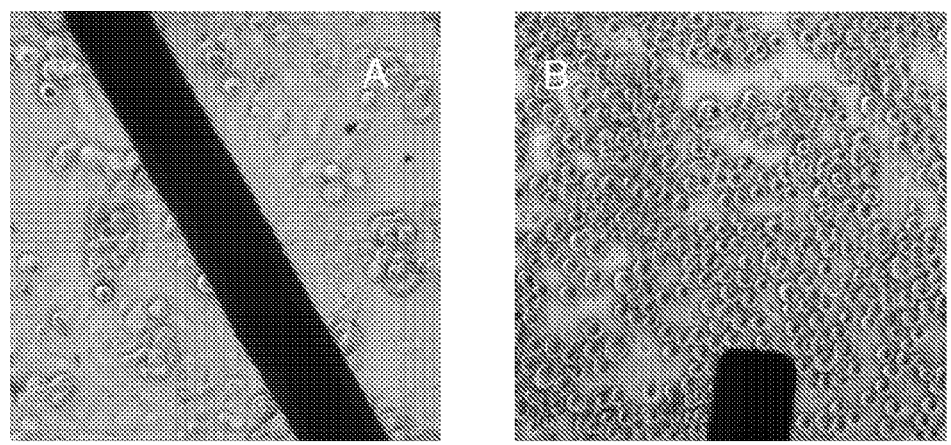
FIG. 25 depicts microphotographs of cells on electrodes for OvCa429 cells (a) after trypsinization and (b) confluent cell layer.

The available ionic charge depends on the concentration of ionic species at any given point, which is dependent upon the rate of consumption and metabolism by the cells. The physical obstruction to the flow of the ions stems from the close approach of anchorage-dependent cells to the substrate, whereby the ions have to circumvent the cells at low frequencies to travel to the counter electrode. Thus, the spreading resistance is an indicator of cell metabolism The electrode-to-electrode variability of the parameters for the eight electrodes emphasizes the ability of the device in resolving cellular behavior in the culture subspace. Microphotograph images of the cell culture confirm the ability of the device to resolve cell confluence for both sparse-density cell cultures after trypsinization, seen in FIG. 25(a), and heavy-density cell cultures, seen in FIG. 23(b). The fact that the confluent culture is not stagnant but continuous motion also contributes toward the variability of these parameters in time and space. In addition, the electrode arrays used in this study were manufactured and assembled separately which also introduce a small device-to-device variability of parameters.

A fully automated system for impedance recording, data acquisition, analysis, visualization and parameter estimation has been implemented for monitoring in-vitro behavior of OvCa429 ovarian cancer cells. The parameter representing cell layer resistance shows clear trends during confluence and cell detachment. The $CPE_{cell}$ magnitude and power factor parameters are more sensitive to cell layer non-uniformity. The scalability of the system to higher number of electrodes may result in improved sensitivity for cell behavior monitoring. In addition to quantitative parameterization of cell behavior, several 2D and 3D visualization options are available in the software package. The multielectrode scans can also provide statistical correlation.

It is also to be understood that the following claims are intended to cover all of the generic and specific features of the invention herein described, and all statements of the scope of the invention which, as a matter of language, might be said to fall therebetween. Now that the invention has been described, What is claimed is:

1. A device for impedance measurement comprising:
   a substrate having an upper face and a lower face;
   a plurality of planar test electrodes disposed in a radial array on the upper face of the substrate, wherein each electrode consists essentially of gold having a diameter ranging from 50 μm to 500 μm, and wherein each test electrode terminates in planar electrode tip, wherein the electrode tip is thicker than the rest of the test electrode due to a thick layer of gold on the electrode tip;
   a cloning cylinder having an upper edge and a lower edge, wherein the lower edge is mounted to the upper face of the substrate, wherein the cloning cylinder defines an interior culturing space;
      wherein at least a portion of the test electrodes extend into the interior culturing space;
   a counter electrode mounted to the upper face of the substrate and disposed in the interior culturing space and out-of-plane with the test electrodes;
   a switching circuit in electrical contact with the test electrodes wherein the switching circuit is comprised of
      a counter;

a decoder;
an inverter;
a plurality of reed relays;
and a plurality of LEDs; and
an AC power source, wherein the power source is adapted to alter the frequency of the AC current applied to the test electrodes.

2. The device of claim 1, wherein the frequency of the AC current applied to the test electrodes is between 1 hertz and 100 megahertz.

3. The device of claim 1, further comprising a two-port impedance measurement device.

4. The device of claim 3, wherein the two-port impedance measurement device is selected from the group consisting of a potentiostat/galvanostat, and an impedance analyzer.

5. The device of claim 1, further comprising a switching board electrically connected to the electrodes.

6. The device of claim 1, further comprising analysis software wherein impedance data from the plurality of electrodes collected at multiple frequencies at the same time is superimposed to form a single scan dataset.

7. The device of claim 1, wherein the switching circuit is a printed circuit board.

8. The device of claim 1, wherein the device comprises 8 test electrodes.

9. The device of claim 1, wherein the test electrodes have a diameter selected from the group consisting of 50 μm, 100 μm, 250 μm, and 500 μm.

10. The device of claim 1, wherein the plurality of test electrodes are coated in a polymer coating, wherein the polymer coating is a hydrophobic coating or SU-8.

11. The device of claim 1, wherein the plurality of test electrodes are electroplated or surface roughened.

12. The device of claim 1, wherein the plurality of test electrodes are 5000 μm in length and wherein approximately 2500 μm of the electrode is disposed in the interior space of the cloning cylinder.

13. The device of claim 1, wherein the electrodes have an average thickness of approximately 1.7 μm.

14. The device of claim 1, wherein the electrode tip has a thickness of approximately 4 μm.

15. The device of claim 1, wherein the counter electrode comprises a brass core and gold coating.

16. The device of claim 1, wherein the counter is a decade ripple counter.

17. The device of claim 1, wherein the decoder is a 3 to 8 decoder.

18. A method of analyzing cell culture characteristics, comprising:
providing a sample of test cells
providing a cell impedance testing device comprising:
a plurality of planar test electrodes disposed in a radial array;
a cloning cylinder mounted to the upper surface of the test electrodes;
a counter electrode mounted to the cloning cylinder and out-of-plane with the eight electrodes;
switching circuit in electrical contact with the test electrodes;
incubating the test cells in the testing device;
obtaining electrical impedance data from the test cells using the testing device; and
extracting impedance information from the cells selected from the group consisting of Interfacial capacitance cell-junctional resistance, dipole rotations, polarization.

19. The method of claim 18, wherein the cellular characteristics are selected from the group consisting of directionality of cell motion, cell growth, cell attachment, cell spreading, confluence, apoptosis, and cell density distribution.

20. The method of claim 18, further comprising importing data from the device into a computer program and converting the data into time frames.

21. The method of claim 18, wherein the test cells were incubated for 2 hours prior to obtaining electrical impedance data.

22. The method of claim 18, wherein the electrical impedance data is obtain using electricity frequency between 1 hertz and 100 megahertz.

23. The method of claim 18, wherein the cell impedance testing device uses 8 test electrodes.

\* \* \* \* \*

UNITED STATES PATENT AND TRADEMARK OFFICE
CERTIFICATE OF CORRECTION

| | |
|---|---|
| PATENT NO. | : 9,121,806 B1 |
| APPLICATION NO. | : 12/180982 |
| DATED | : September 1, 2015 |
| INVENTOR(S) | : Shekhar Bhansali and Abdur Rub Abdur Rahman |

It is certified that error appears in the above-identified patent and that said Letters Patent is hereby corrected as shown below:

In the Specification

Column 1, lines 14-19 should read:

STATEMENT OF GOVERNMENT SUPPORT

This invention was made with government support under Grant Number 2106037 awarded by the National Science Foundation. The government has certain rights in the invention.

Signed and Sealed this
Eighth Day of March, 2016

Michelle K. Lee
*Director of the United States Patent and Trademark Office*